United States Patent [19]

Fisher et al.

[11] Patent Number: 5,451,677
[45] Date of Patent: Sep. 19, 1995

[54] SUBSTITUTED PHENYL SULFONAMIDES AS SELECTIVE β 3 AGONISTS FOR THE TREATMENT OF DIABETES AND OBESITY

[75] Inventors: Michael H. Fisher, Ringoes; Robert J. Mathvink, Jersey City; Hyun O. Ok, Edison; Emma R. Parmee, Hoboken; Ann E. Weber, Scotch Plains, all of N.J.

[73] Assignee: Merck & Co., Inc., Rahway, N.J.

[21] Appl. No.: 168,105

[22] Filed: Dec. 15, 1993

Related U.S. Application Data

[63] Continuation-in-part of Ser. No. 15,689, Feb. 9, 1993, abandoned.

[51] Int. Cl.$^6$ .................. C07D 455/00; C07D 307/10; C07C 311/01
[52] U.S. Cl. .................. 546/138; 546/290; 548/316.4; 548/469; 548/541; 549/33; 549/416; 549/475; 564/80; 564/82; 564/83; 564/84; 564/85; 564/86; 564/87; 564/88; 564/89; 564/90; 564/92; 564/96; 564/99
[58] Field of Search .................. 514/604, 605; 564/80, 564/82, 83, 84, 85, 86, 87, 88, 89, 90, 92, 96, 99; 546/290, 138; 548/469, 541, 316.4; 549/33, 475, 416

[56] References Cited

U.S. PATENT DOCUMENTS

| | | | |
|---|---|---|---|
| 4,083,992 | 4/1978 | Smith . | |
| 4,396,627 | 8/1983 | Ainsworth et al. | 514/533 |
| 4,478,849 | 10/1984 | Ainsworth et al. | 514/445 |
| 4,959,366 | 9/1990 | Cross et al. | 514/239.5 |
| 4,999,377 | 3/1991 | Caulkett et al. | 514/507 |
| 5,017,619 | 5/1991 | Alig et al. | 514/653 |
| 5,066,678 | 11/1991 | Skidmore et al. | 514/597 |
| 5,153,210 | 10/1992 | Ainsworth et al. | 514/369 |

FOREIGN PATENT DOCUMENTS

| | | |
|---|---|---|
| 091749 | 10/1983 | European Pat. Off. . |
| 455006 | 4/1991 | European Pat. Off. . |
| 427480 | 5/1991 | European Pat. Off. . |
| 9000548 | 1/1990 | WIPO . |
| 90/15203 | 12/1990 | WIPO . |
| WO94/03425 | 2/1994 | WIPO . |

OTHER PUBLICATIONS

Lis, et al, Abstract to "Synthesis of novel (aryloxy) propanolamines and related compounds possessing both class II and class III antiarrhythmic activity" J. Med. Chem., (1990), 33(10), pp. 2883–2891.
Bloom, et al., J. Med. Chem., 35 3081–3084 (1992).
Still, et al., J. Org. Chem., 43, 2923 (1978).

*Primary Examiner*—José G. Dees
*Assistant Examiner*—Dwayne C. Jones
*Attorney, Agent, or Firm*—Mollie M. Yang; David L. Rose

[57] ABSTRACT

Substituted phenylsulfonamides are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. The compounds are prepared by coupling an aminoalkylphenyl-sulfonamide with an appropriately substituted alkyl epoxide. Compositions and methods for the use of the compounds in the treatment of diabetes and obesity and for lowering triglyceride levels and cholesterol levels or raising high density lipoprotein levels or for increasing gut motility are also disclosed.

18 Claims, No Drawings

SUBSTITUTED PHENYL SULFONAMIDES AS SELECTIVE β 3 AGONISTS FOR THE TREATMENT OF DIABETES AND OBESITY

CROSS REFERENCE TO RELATED APPLICATIONS

This application is a continuation-in-part of our application Ser. No. 08/015,689 filed Feb. 9, 1993, abandoned on May 12, 1994.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxtion ($\beta_2$)- These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectively, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett etal., U.S. Pat. No. 4,999,377, Alig et al., U.S. Pat. No. 5,017,6 19, Lecount et al., European Patent 427480 and Bloom et al., European Patent 455006.

Even though these more recent developments purport to describe compounds with greater $\beta_3$ selectively over the $\beta_1$ and $\beta_2$ activities, this selectively was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. The agonist and antagonist effects of the various compounds on the cultivated cells provide an indication of the antiobesity and antidiabetic effects of the compounds in humans.

SUMMARY OF THE INVENTION

The instant invention is concerned with substituted phenyl sulfonamides which are useful as antiobesity and antidiabetic compounds. Thus, it is an object of this invention to describe such compounds. It is a further object to describe the specific preferred stereoisomers of the substituted phenylsulfonamides. A still further object is to describe processes for the preparation of such compounds. Another object is to describe methods and compositions which use the compounds as the active ingredient thereof. Further objects will become apparent from reading the following description.

DESCRIPTION OF THE INVENTION

The compounds of the instant invention are best realized in the following structural formula:

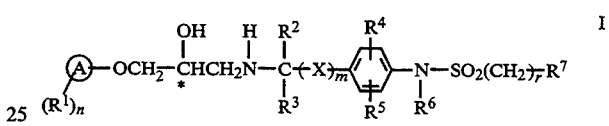

where
n is 0 to 7;
m is 0 or 1;
r is 0 to 3;
A is phenyl, naphthyl, a 5 or 6-membered heterocyclic ring with from 1 to 4 heteroatoms selected from oxygen, sulfur or nitrogen, a benzene ring fused to a $C_3$-$C_8$ cycloalkyl ring, a benzene ting fused to a 5 or 6-membered heterocyclic ring with from 1 to 3 heteroatoms selected from oxygen, sulfur or nitrogen or a 5 or 6-membered heterocyclic ring with from 1 to 3 heteroatoms selected from oxygen, sulfur or nitrogen fused to a 5 or 6-membered heterocyclic ting with from 1 to 3 heteroatoms selected from oxygen, sulfur or nitrogen;
$R^1$ is hydroxy, oxo, halogen, cyano, nitro, $NR^8R^8$, $SR^8$, trifluoromethyl, $C_1$-$C_6$ alkyl, $C_1$-$C_6$ alkoxy, $C_3$-$C_8$ cycloalkyl, phenyl, $SO_2R^9$, $NR^8COR^9$, $COR^9$, $NR^8SO_2R^9$, $NR^8CO_2R^8$ or $C_1$-$C_6$ alkyl substituted by hydroxy, nitro, halogen, cyano, $NR^8R^8$, $SR^8$, trifluoromethyl, $C_1$-$C_6$ alkoxy, $C_3$-$C_8$ cycloalkyl, phenyl, $NR^8COR^9$, $COR^9$, $SO_2R^9$, $NR^8SO_2R^9$, $NR^8CO_2R^8$, or $R^1$ is a 5 or 6-membered heterocycle with from 1 to 3 heteroatoms selected from oxygen, sulfur or nitrogen;
$R^2$ and $R^3$ are independently hydrogen, $C_1$-$C_6$ alkyl or $C_1$-$C_6$ alkyl substituted by 1 to 3 of hydroxy, $C_1$-$C_6$ alkoxy, or halogen;
X is —$CH_2$—, —$CH_2$—$CH_2$—, —CH=CH— or —$CH_2O$—;
$R^4$ and $R^5$ are independently hydrogen, $C_1$-$C_6$ alkyl, halogen, $NHR_8$, $OR_8$, $SO_2R^9$ or $NHSO_2R^9$;
$R^6$ is hydrogen or $C_1$-$C_6$ alkyl;
$R^7$ is $C_1$-$C_6$ alkyl, $C_3$-$C_8$ cycloalkyl, or B-(RI)n;
B is phenyl, naphthyl, a 5 or 6-membered heterocyclic ring with from 1 to 4 heteroatoms selected from oxygen, sulfur or nitrogen, a benzene ring fused to a $C_3$-$C_8$ cycloalkyl ring, a benzene ting fused to a 5 or 6-membered heterocyclic ring with from 1 to 3 heteroatoms selected from oxygen, sulfur or nitrogen or a 5 or 6-membered heterocyclic ring with from 1 to 3 heteroatoms selected from oxygen, sulfur or nitrogen fused to a 5 or 6-membered heterocyclic ring with from 1 to 3 heteroatoms selected from oxygen, sulfur or nitrogen;

$R^8$ is hydrogen, $C_1$-$C_{10}$ alkyl, $C_3$-$C_8$ cycloalkyl, phenyl optionally substituted by 1 to 3 of halogen, $C_1$-$C_6$ alkyl or $C_1$-$C_6$ alkoxy, or $C_1$-$C_{10}$ alkyl substituted by 1 to 3 of hydroxy, halogen, $CO_2H$, $CO_2$—$C_1$—$C_6$ alkyl, $C_3$-$C_8$ cycloalkyl, $C_1$-$C_6$ alkoxy, or phenyl optionally substituted by from 1 to 3 of halogen, $C_1$-$C_6$ alkyl or $C_1$-$C_6$ alkoxy;

$R^9$ is $R^8$, $NHR^8$ or $NR^8R^8$.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

The preferred 5 and 6-membered heterocycles and fused heterocycles of A, B and $R_1$ are those heterocycles with from 1 to 4 heteroatoms independently selected from one of oxygen or sulfur or 1 to 4 nitrogen atoms.

The preferred values of A and B are phenyl, naphthyl or the foregoing preferred 5 and 6-membered heterocycles and fused heterocycles.

The more preferred values of A are phenyl, naphthyl, pyridyl, quinolinyl, pyrimidinyl, pyrrollyl, thienyl, imidazolyl, and thiazolyl.

The more preferred values of B are phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzisoxazolyl, benzothiazolyl, tetrahydronaphthyl, dihydrobenzofuranyl, and tetrahydroquinolinyl.

Further preferred compounds of the instant invention are s realized when in the above structural formula:

$R^2$ and $R^3$ are hydrogen or methyl;
X is —$CH_2$—
m is 1;
r is 0–2; and
$R^4$, $R^5$ and $R^6$ are hydrogen.

Still further preferred compounds of the instant invention are realized when in the above structural formula:

A is phenyl, quinolinyl, or a 6-membered heterocyclic ring with 1 or 2 nitrogen atoms;
B is phenyl or quinolinyl;
$R^1$ is $NH_2$, hydroxy, halogen, cyano, trifluoromethyl, phenyl, $NR^8COR^9$, $NR^8CO_2R^8$, $C_1$-$C_6$ alkyl optionally substituted by hydroxy; and
r is 0or2.

Representative preferred antiobesity and antidiabetic compounds of the present invention include the following: N-[4-[2-[[2-hydroxy-3-(4-hydroxyphenoxy)propyl]amino]ethyl]phenyl]benzenesulfonamide N-[4-[2-[[2-hydroxy-3-(4-hydroxyphenoxy)propyl]amino]ethyl]phenyl]-4-iodobenzenesulfonamide N-[4-[2-[[2-hydroxy-3-(4-hydroxyphenoxy)propyl]amino]ethyl]phenyl]-2-naphthalenesulfonamide N-[4-[2-[[2-hydroxy-3-(4-hydroxyphenoxy)propyl]amino]ethyl]phenyl]4-(benzo-2,1,3-thiadiazole)sulfonamide N-[4-[2-[[2-hydroxy-3-(4-hydroxyphenoxy)propyl]amino]ethyl]phenyl]-2-phenylethanesulfonamide N-[4-[2-[[3-(4-fluorophenoxy)-2-hydroxypropyl]amino]ethyl]phenyl]-4-benzenesulfonamide N-[4-[2-[[3-[(2-amino-5-pyridinyl)oxy]-2-hydroxyptopyl]amino]ethyl]phenyl]-2-naphthalenesulfonamide N-[4-[2-[[2-hydroxy-3-(4-hydroxyphenoxy)propyl]amino]ethyl]phenyl]-3-quinolinesulfonamide N-[4-[2-[[2-hydroxy-3-(4-hydroxyphenoxy)propyl]amino]ethyl]phenyl]-4-[(5-methoxycarbonyl)pentanoyl]amino]benzenesulfonamide N-[4-[2-[[2-hydroxy-3-(4-hydroxyphenoxy)propyl]amino]ethyl]phenyl]-4-[(5-hydroxycarbonyl)pentanoyl]amino]benzenesulfonamide N-[4-[2-[[2-hydroxy-3-(4-hydroxyphenoxy)propyl]amino]ethyl]phenyl]-4-(hexylaminocarbonylamino)benzenesulfonamide N-[4-[2-[(2-hydroxy-3-phenoxypropyl)amino]ethyl]phenyl]-4-chlorobenzenesulfonamide N-[4-[2-[[2-hydroxy-3-(3-cyanophenoxy)propyl]amino]ethyl]phenyl]-3-quinolinesulfonamide N-[4-[2-[[3-(4-amino-3-cyanophenoxy)-2-hydroxypropyl]amino]ethyl]phenyl ]-3-quinolinesulfonamide N-[4-[2-[[2-hydroxy-3-[(3-hydroxymethyl)phenoxy]propyl]amino]ethyliphenyl]-3-quinolinesulfonamide N-[4-[2-[[2-hydroxy-3-(3-pyridyloxy)propyl]amino]ethyl]phenyl]-3-quinolinesulfonamide N-[4-[2-[[2-hydroxy-3-(3-pyridyloxy)propyl]amino]ethyl]phenyl]-4-iodobenzenesulfonamide N-[4-[2-[[3-[(2-amino-5-pyridinyl)oxy]-2-hydroxypropyl]amino]ethyl]phenyl]-4-isopropylbenzenesulfonamide.

The compounds of the instant invention all have at least one asymmetric center as noted by the asterisk in structural Formulae I and Ia. Additional asymmetric centers may be present on the molecule depending upon the nature of the various substituents on the molecule, in particular, $R_2$ and $R_3$. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the hydroxy substituent is above the plane of the structure, as seen in Formula Ia, is more active and thus more preferred over the compound in which the hydroxy substituent is below the plane of the structure.

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The following stereospecific structure represents the preferred stereoisomers of the instant invention.

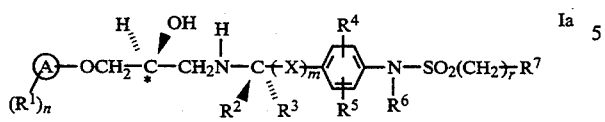

pos where the various substituents are as defined above.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

The compounds (I) of the present invention can be prepared from epoxide intermediates such as those of formula II and amine intermediates such as those of formula III. The preparation of these intermediates is described in the following schemes.

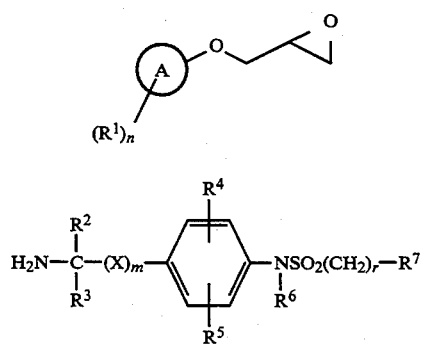

where n, m, r, A, $R_1$, $R_2$, $R_3$, $R_4$, $R_5$, $R_6$, $R_7$ and X are as defined above.

Compounds II can be conveniently prepared by a variety of methods familiar to those skilled in the art. One common route is illustrated in Scheme 1. Alcohol 1 is treated with base such as sodium hydride or potassium t-butoxide in a polar solvent such as anhydrous dimethylformamide. The resultant anion is alkylated with epoxide derivative 2, wherein "L" is a leaving group such as a sulfonate ester or a halide, for 0.5 to 24 hours at temperatures of 20°–100° C. to provide compound II. The epoxide derivative 2 is conveniently the commercially available, enantiomerically pure (2S) or (2R)-glycidyl 3-nitrobenzene sulfonate or (2R) or (2S)-glycidyl 4-toluenesulfonate, thus both the (S) and (R) enantiomers of epoxide II are readily available.

SCHEME 1

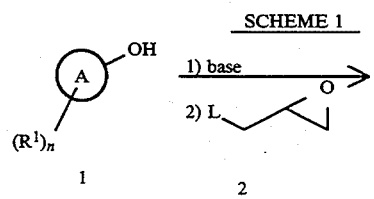

-continued
SCHEME 1

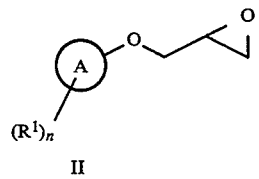

Many of the alcohols 1 are commercially available or readily prepared by methods described in the literature and known to those skilled in the art. $R^1$ substituents on the alcohol 1 may need to be protected during the alkylation and subsequent procedures. A description of such protecting groups may be found in: *Protective Groups in Organic Synthesis*, 2nd Ed., T. W. Greene and P. G. M. Wuts, John Wiley and Sons, New York, 1991. A useful method for protecting the preferred alchohol 1 wherein A ($R^1$)$_n$ is 4-hydroxyphenyl as its tert-butyldimethylsilyl (TBS) derivative is illustrated in Scheme 2. Commercially available phenol 3 is treated with a silylating agent such as tert-butyldimethylsilyl chloride in the presence of a base such as imidazole in an aprotic solvent such as dimethylformamide. The benzyl group is then removed by catalytic hydrogenation to give the desired alcohol 5.

SCHEME 2

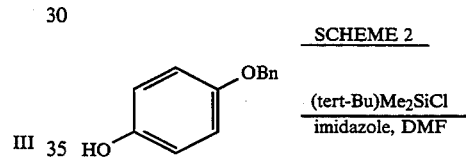

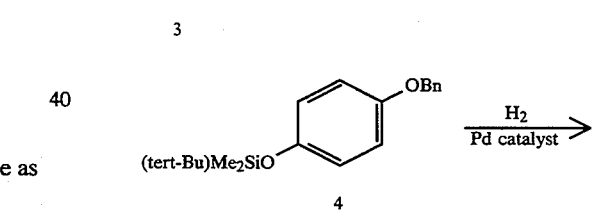

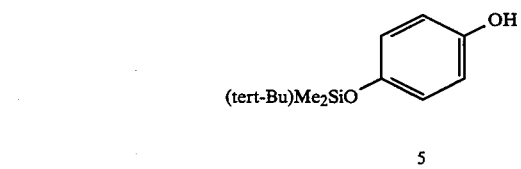

Compounds III can be conveniently prepared by a variety of methods familiar to those skilled in the art. A convenient route for their preparation when $R^6$ is hydrogen is illustrated in Scheme 3. Compound 6 is selectively protected as a suitable carbamate derivative 6a with, for example, di-tert-butyl dicarbonate or carbobenzyloxy chloride. This compound is then treated with a sulfonyl halide, preferably the sulfonyl chloride 7, and a base such as pyridine in an anhydrous solvent such as dichloromethane or chloroform for 0.5 to 24 hours at temperatures of −20° to 50° C., preferably 0° C., to provide the sulfonamide 8. The protecting group is then removed with, for example, trifluoroacetic acid in the case of Boc or catalytic hydrogenation in the case of Cbz, to give the desired amine 9.

SCHEME 3

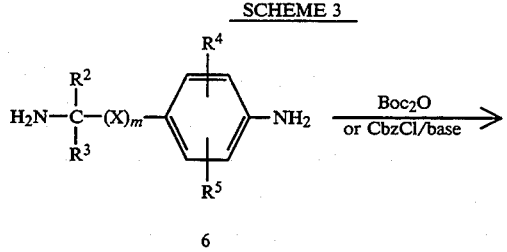

6

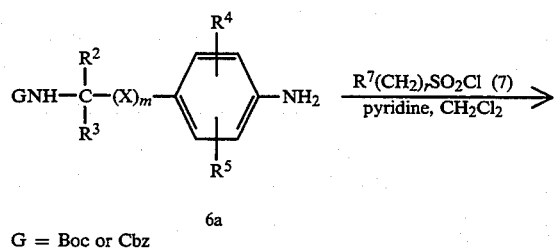

6a

G = Boc or Cbz

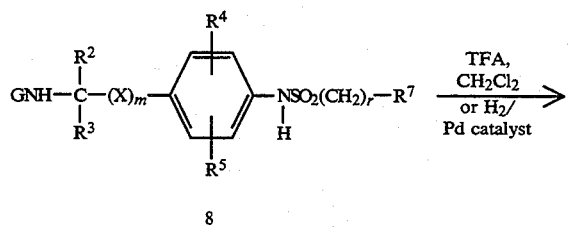

8

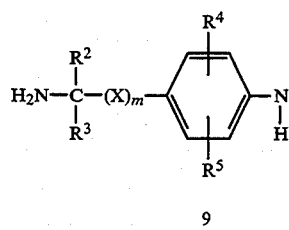

9

Compounds III where $R^6$ is not hydrogen may be conveniently prepared as illustrated in Scheme 4. Sulfonamide 8, prepared as described above, is alkylated with an appropriate alkylating agent 10 in the presence of base to provide sulfonamide 11. Removal of the protecting group as above gives the desired compound III.

SCHEME 4

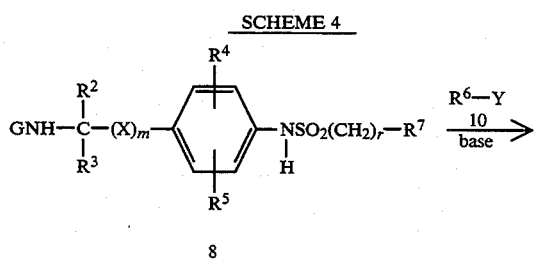

8

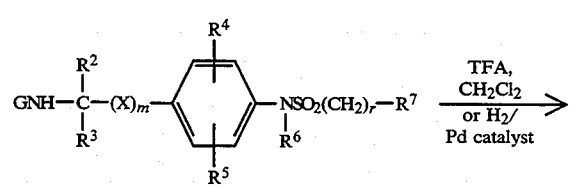

11

-continued
SCHEME 4

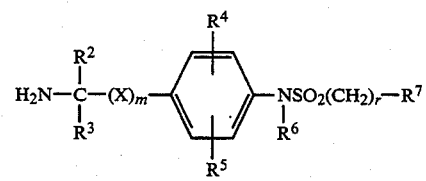

G = Boc or Cbz
Y = Cl, Br, or I   III

The sulfonyl chlorides 7, many of which are commercially available, can also be readily prepared by a number of methods familiar to those skilled in the art. One suitable method involves the addition of an organolithium reagent or a Grignard reagent to sulfuryl chloride following the procedure of S. N. Bhattacharya, et. al., J. Chem. Soc. (C), 1265–1267 (1968). Another convenient method involves the treatment of a thiol with sulfuryl chloride and a metal nitrate according to the procedure of Y. J. Park, et. al., Chemistry Letters, 1483–1486 (1992). Sulfonic acids are also conveniently converted to the corresponding sulfonyl chloride by treatment with $PCl_5$, $PCl_3$ or $SOCl_2$ (J. March, Advanced Organic Chemistry, 4th Ed., John Wiley and Sons, New York: 1992, p 1297 and references cited therein). Alternatively, aromatic compounds may be treated with chlorosulfonic acid according to the procedure of Albert, et. al., J. Het. Chem. 15, 529 (1978), to provide the sulfonyl chlorides.

The diamines 6 are commercially available or readily prepared by methods described in the literature or known to those skilled in the art. Compound 6 where $R^2$ or $R^3$ is methyl can be prepared from the corresponding amino acid following the method of J. D. Bloom, et. al., J. Med. Chem., 35, 3081–3084 (1992). As illustrated in Scheme 5 for $R^3$=methyl, the appropriate (R) amino acid 12 is esterified, conveniently by treatment with methanolic hydrochloric acid, and then treated with di-tert-butyl dicarbonate to give compound 13. The ester group is reduced with a hydride source such as lithium borohydride and the resultant alcohol is converted to a leaving group such as a mesylate. Removal of the Boc protecting groups gives diamine 14. This compound is subjected to catalytic hydrogenation in the presence of base such as sodium acetate to give the desired a-methyl amine 15. The other enantiomer is available through an analogous sequence starting with the corresponding (S) amino acid.

SCHEME 5

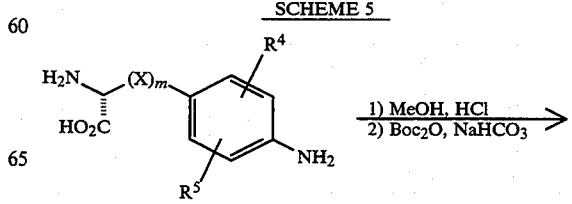

12

-continued
SCHEME 5

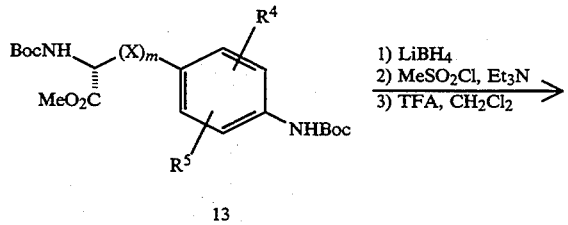

13

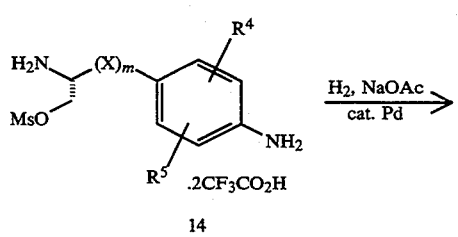

14

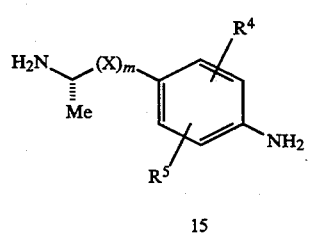

15

Diamines 6 or sulfonamide amines 9 where X is —CH$_2$O— and m is 1 are also readily prepared by methods described in the literature or known to those skilled in the art. For example, as shown in Scheme 6, the sodium salt of 4-nitrophenol 16 is alkylated with 1-bromo-2-chloroethane, conveninetly in refluxing 2-butanone with a base o such as potassium carbonate, to give chloro derivative 17. The chloride is converted to the corresponding amine by treatment with lithium azide followed by reduction with, for example, triphenylphosphine in aqueous tetrahydrofuran. Protection of the resultant amine, conveniently as its t-butyl carbamate by treatment with di-tert-butyldicarbonate, gives derivative 18. The nitro group is then reduced, for example, by catalytic hydrogenation to provide amine 19. Acylation of intermediate 19 with sulfonyl chloride 7, followed by deprotection with acid such as trifluoroacetic acid gives the desired intermediate 20.

SCHEME 6

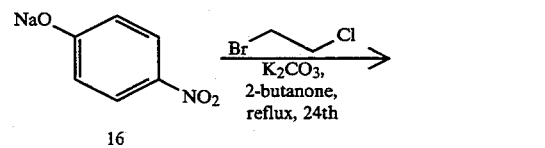

16

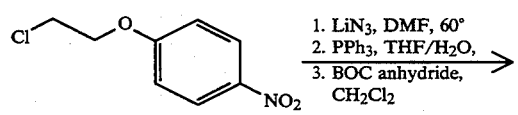

17

-continued
SCHEME 6

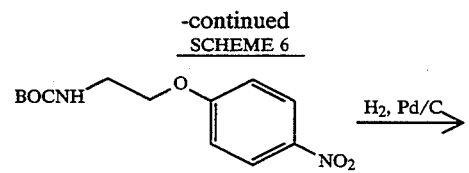

18

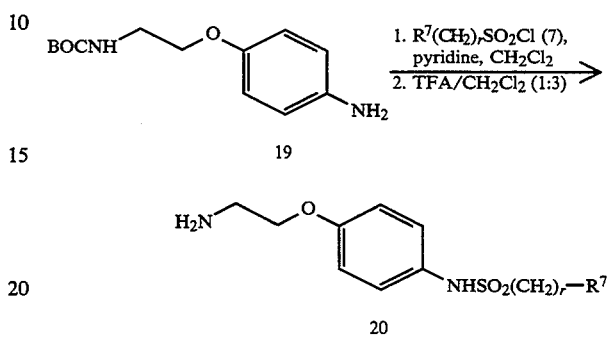

19

20

Alternatively, diamine 6 where X is —CH$_2$O— and m is 1 is available from intermediate 19 by treatment with trifluoroacetic acid. This diamine may then be modified as illustrated in Scheme 3.

Diamines 6 and sulfonamide amines 9 where X is —CH$_2$CH$_2$— and m is I are also readily prepared by methods described in the literature or known to those skilled in the art. For example, as shown in Scheme 7, bromo derivative 21 is treated with sodium cyanide to provide nitrile 22. The nitro group is selectively reduced by treatment with hydrogen and catalytic palladium to provide amine 23. Amine 23 is acylated with sulfonyl chloride 7 to give the corresponding sulfonamide 24. Reduction of compound 24 with cobalt chloride and sodium borohydride provides the desired amine 25.

SCHEME 7

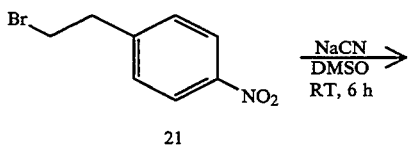

21

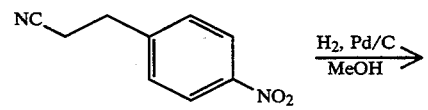

22

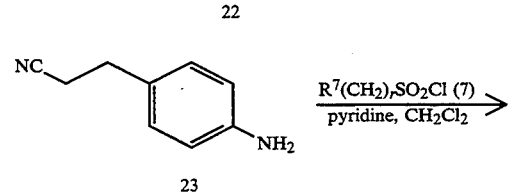

23

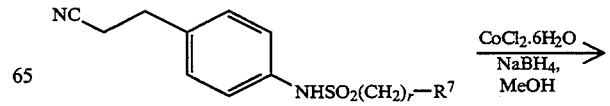

24

-continued
SCHEME 7

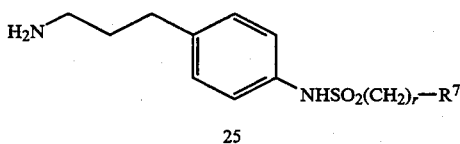

25

Alternatively, diamine 6 where X is —CH$_2$CH$_2$— and m is 1 is available from intermediate 23 by reduction of the nitrile group with, for example, cobalt chloride and sodium borohydride. This diamine may then be modified as illustrated in Scheme 3.

Intermediates II and III are coupled by heating them neat or as a solution in a polar solvent such as methanol, acetonitrile, tetrahydrofuran, dimethylsulfoxide or N-methyl pyrrolidinone for 1 to 24 hours at temperatures of 30° to 150° C. to provide compounds I as shown in Scheme 8. The reaction is conveniently conducted in refluxing methanol. Alternatively, a salt of amine III, such as the trifluoroacetate or hydrochloride salt, may be used. In these cases, a base such as sodium bicarbonate or diisopropylethylamine is added to the reaction mixture. The product is purified from unwanted side products by recrystallization, trituration, preparative thin layer chromatography, flash chromatography on silica gel as described by W. C. Still, et. al., *J. Org. Chem.* 43, 2923 (1978), medium pressure liquid chromatography, or HPLC. Compounds which are purified by HPLC may be isolated as the corresponding salt. Purification of intermediates is achieved in the same manner.

SCHEME 8

-continued
SCHEME 8

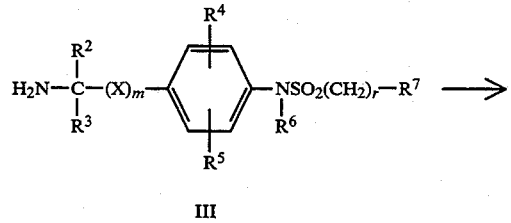

III

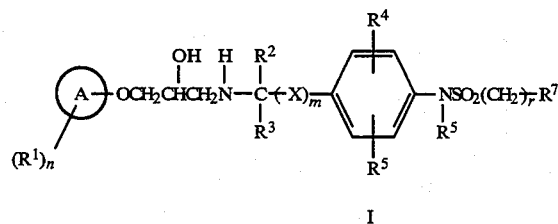

I

In some cases, the coupling product I from the reaction described in Scheme 8 may be further modified, for example, by the removal of protecting groups or the manipulation of substituents on, in particular, R$^1$ and R$^7$. These manipulations may include reduction, oxidation, alkylation, acylation, and hydrolysis reactions which are commonly known to those skilled in the art. One such example is illustrated in Scheme 9. Compound 26, which is prepared as outlined in the Scheme 8 from the corresponding epoxide, is subjected to catalytic hydrogenation in a polar solvent such as 1:1 acetic acid/methanol to provide compound 27. Other examples of substituents on compound I which may be reduced to the corresponding amine by catalytic hydrogenation and methods commonly known to those skilled in the art include nitro groups, nitriles, and azides.

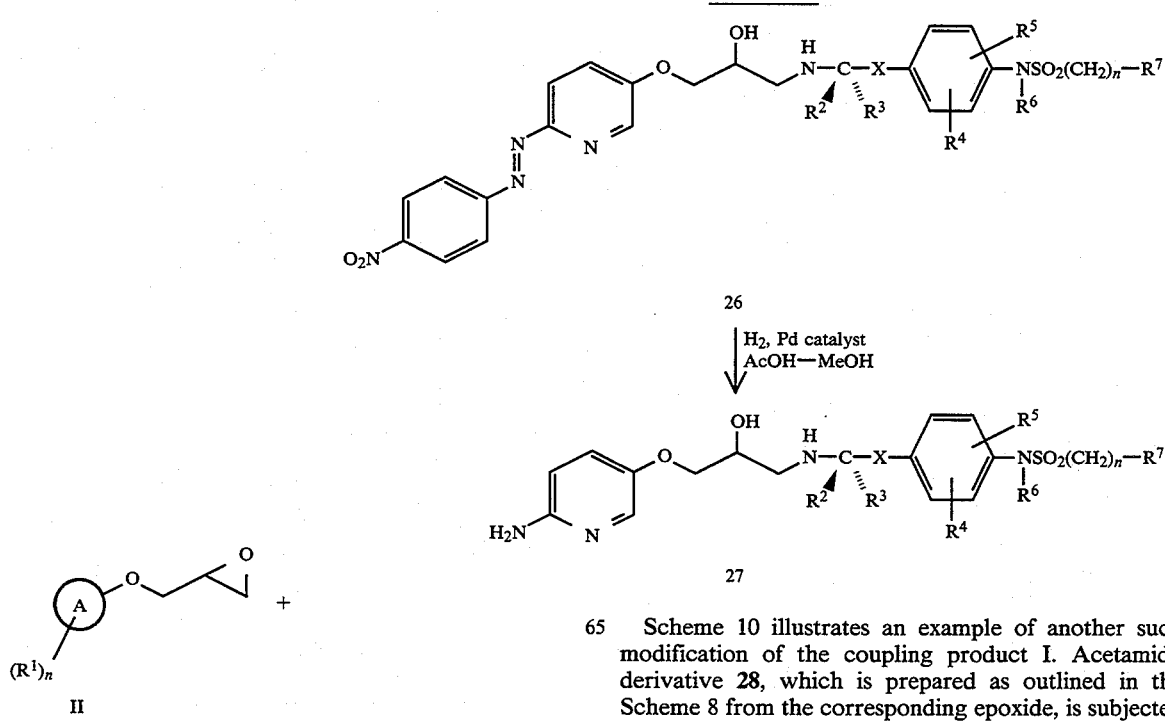

Scheme 10 illustrates an example of another such modification of the coupling product I. Acetamido derivative 28, which is prepared as outlined in the Scheme 8 from the corresponding epoxide, is subjected to hydrolysis in a protic solvent such as methanol/water with added acid or base such as hydrochloric acid or sodium hydroxide to provide the corresponding aniline derivative 29.

chloride in the presence of a base such as pyridine followed by removal of the protecting group with, in the case of a tert-butylcarbamate, acid such as trifluoroacetic acid or methanolic hydrogen chloride, provides the

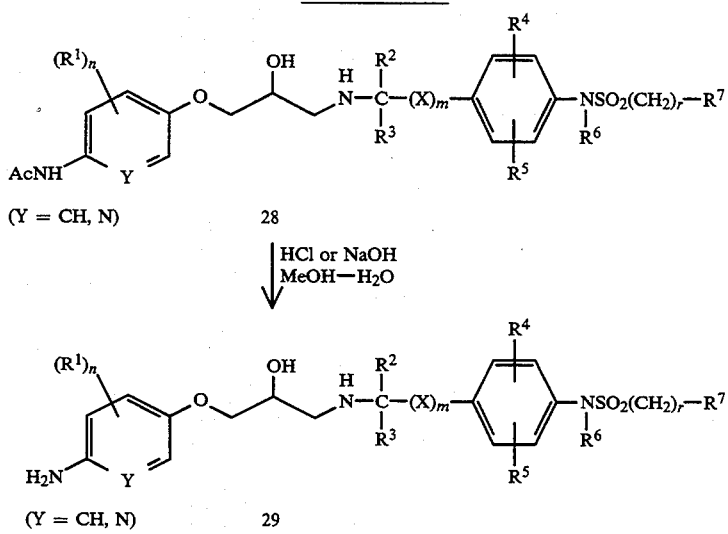

An alternate method for the synthesis of compound I sulfonamide I.

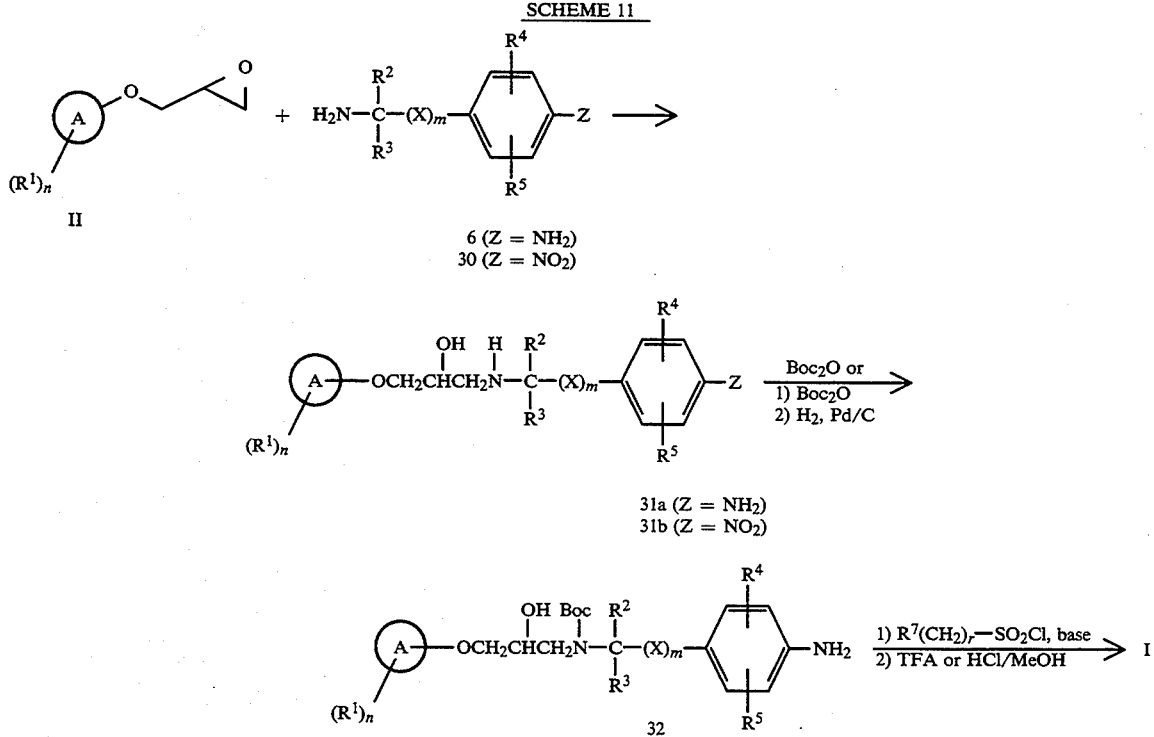

is illustrated in Scheme 11. Epoxide II is coupled to amine 6 as described above for coupling intermediates II and III (Scheme 8) to give aniline derivative 31a. The secondary amine is selectively protected, for example, as a carbamate by treatment with di-tert-butyldicarbonate to provide carbamate 32. Alternatively, nitro amine 30 is used in the coupling reaction to provide 31b. Following protection as described above, the nitro group is reduced, for example, by catalytic hydrogenation, to provide intermediate 32. Treatment with a sulfonyl In some cases, sulfonamide I from the reaction sequence illustrated in Scheme 11 may be further modified, for example, by the removal of protecting groups or the manipulation of substituents on, in particular, $R^1$ and $R^7$, as described above. In addition, manipulation of substituents on any of the intermediates in the reaction sequence illustrated in Scheme 11 may occur. An example of this is illustrated in Scheme 12. N-Boc 4- nitrobenzenesulfonamide 33, which is prepared from intermediate 32 and 4-nitrobenzenesulfonyl chloride, is subjected to catalytic hydrogenation and the resultant aniline is acylated with, for example, an acid chloride in the presence of base to give N-Boc intermediate 34. Deprotection with acid such as trifluoroacetic acid or methanolic hydrogen chloride provides the desired sulfonamide 35.

nous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and

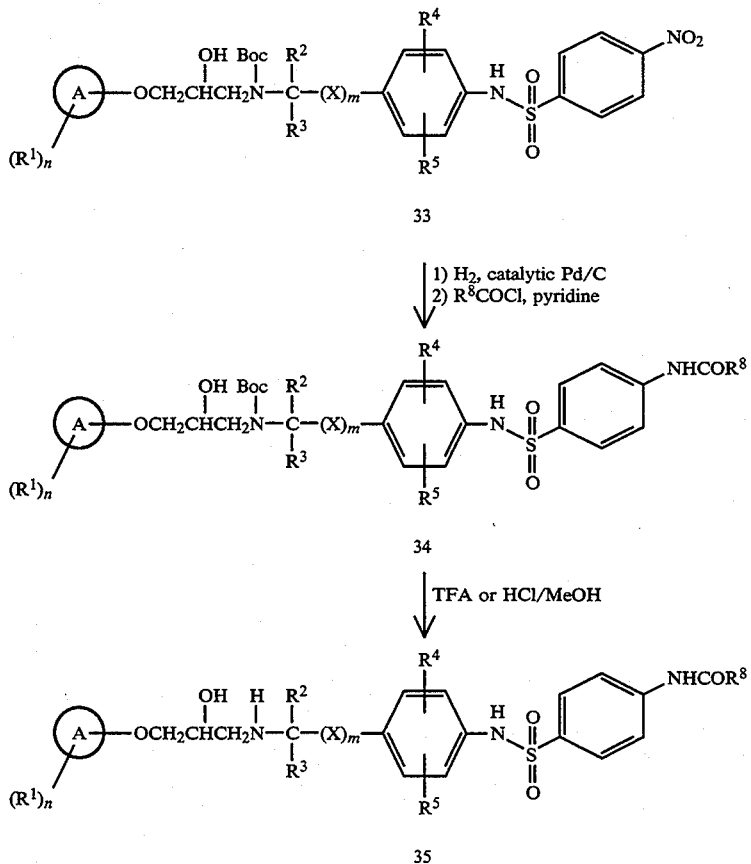

As previously indicated, the compounds of the present invention have valuable pharmacological properties.

The present invention also provides a compound of the general Formula I or a pharmaceutically acceptable salt thereof for use as an active therapeutic substance.

In one aspect, the present invention provides a compound of the general Formula I or a pharmaceutically acceptable ester thereof: or a pharmaceutically acceptable salt thereof for use in the treatment of obesity in human or non-human animals.

The present invention further provides a compound of the general Formula I, or a pharmaceutically acceptable ester thereof; or pharmaceutically acceptable salt thereof, for use in the treatment of hyperglycemia (diabetes) in human or non-human animals.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

appears to be the result of the inability of tissues to respond appropriately to insulin. Most of the Type II diabetics are also obese.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hyper-triglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly, in another aspect the present invention provides a method of lowering triglyceride and/or cholesterol levels and/or increasing high density lipoprotein levels which comprises administering, to an animal in need thereof, a therapeutically effective amount of a compound of the formula (I) or pharmaceutically acceptable salt thereof. In a further aspect the present invention provides a method of treating atherosclerosis which comprises administering, to an animal in need thereof; a therapeutically effective amount of a compound of the formula (I) or pharmaceutically acceptable salt thereof. The compositions are formulated and administered in the same general manner as detailed below for treating diabetes and obesity. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:-cholesterol acyltransferase) inhibitors for example melinamide; anion exchange resins for example cholestyramine, colestipol or a dialkylaminoalkyl derivatives of a cross-linded dextran; nicotinyl alcohol, nicotinic acid or a salt thereof; vitamin E; and thyromimetics.

The compounds of the instant invention also have the effect of reducing intestinal motility and thus find utility as aiding in the treatment of various gastrointestinal disorders such as irritable bowel syndrome. It has been proposed that the motility of non-sphincteric smooth muscle contraction is mediated by activity at $\beta_3$ adrenoreceptors. The availability of a $\beta_3$ specific agonist, with little activity at $\beta_1$ and $\beta_2$ receptors will assist in the pharmacologic control of intestinal motility without concurrent cardiovascular effects. The instant compounds are administered generally as described below with dosages similar to those used for the treatment of diabetes and obesity.

It has also been found unexpectedly that the compounds which act as agonists at $\beta_3$ adrenoreceptors may be useful in the treatment of gastrointestinal disorders, especially peptic ulcerations, esophagitis, gastritis and duodenitis, (including that induced by H. pylori), intestinal ulcerations (including inflammatory bowel disease, ulcerative colitis, Crohn's disease and proctitis) and gastrointestinal ulcerations.

In addition, $\beta_3$ receptors have been indicated to have an effect on the inhibition of the release of neuropeptides in certain sensory fibers in the lung. As sensory nerves may play an important role in the neurogenic inflammation of airways, including cough, the instant specific $\beta_3$ agonists may be useful in the treatment of neurogenetic inflammation, such as asthma, with minimal effects on the cardiopulmonary system.

$\beta_3$ adrenoreceptors are also able to produce selective antidepressant effects by stimulating the $\beta_3$ receptors in the brain and thus an additional contemplated utility of the compounds of this invention are as antidepressant agents.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.1 milligram to about 1 milligram per kilogram of animal body weight, preferably given in divided doses two to six times a day, or in sustained release form. For most large mammals, the total daily dosage is from about 3.5 milligrams to about 140 milligrams, preferably from about 3.5 milligrams to about 5 milligrams. In the case of a 70 kg adult human, the total daily dose will generally be from about 7 milligrams to about 70 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 1 milligram to about 10 milligrams per kilogram of animal body weight, preferably given in divided doses two to six times a day, or in sustained release form. For most large mammals, the total daily dosage is from about 35 milligrams to about 1,400 milligrams, preferably from about 35 milligrams to about 50 milligrams. In the case of a 70 kg adult human, the total daily dose will generally be from about 70 milligrams to about 700 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carder such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, The following examples are provided so that the invention might be more fully understood. They should not be construed as limiting the invention in any way.

EXAMPLE 1

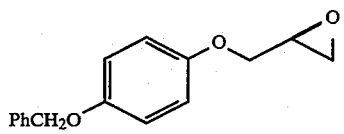

(S)-2-1[(4-Phenylmethoxy)phenloxylmethyl]oxirane

A solution of 1.54 g (7.72 mmol) of 4-benzyloxyphenol in 10 mL of dimethylformamide (DMF) was added dropwise via cannula to a mixture of 310 mg (7.72 mmol) of sodium hydride (60% dispersion in mineral oil). After the mixture was allowed to stir for 1 h, a solution of 2.00 g (7.72 mmol) of (2S)-glycidyl 3-nitrobenzene sulfonate in 10 mL of DMF was added via cannula. The reaction mixture was allowed to stir at room temperature for 4.5 h. It was diluted with ethyl acetate, washed with three portions of water, dried over magnesium sulfate, and concentrated. Purification by flash chromatography (silica gel, 20% ethyl acetate/hexane) gave 1.84 g (93%) of the title compound: $^1$H NMR (200 MHz, CDCl$_3$) δ7.41–7.28 (m, 5H), 6.90–6.80 (sym m, 4H), 4.99 (s, 2H), 4.14 (dd, 1H, J=3.2, 11 Hz), 3.89 (dd, 1H, J=5.6, 11 Hz), 3.29 (m, 1H), 2.86 (t, 1H, J=5.1Hz), 2.71 (dd, 1H, J=2.6, 5.1 Hz); EI MS m/z 256 (M), 165, 91.

EXAMPLE 2

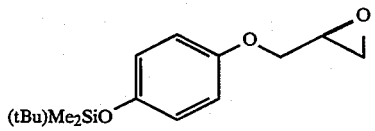

(S)-2-[[4-[[(1,1-Dimethylethyl)dimethylsilyl]oxy]-phenoxy]methyl]oxirane

A solution of 10.0 g (50.0 mmol) of 4-benzyloxyphenol, 9.04 g (60.0 mmol) of tert-butyldimethylsilyl chloride, and 4.42 g (65.0 mmol) of imidazole in dimethylforamide (DMF) was allowed to stir at ambient temperature overnight. The mixture was then diluted with ethyl acetate, washed sequentially with water, 1 M aqueous sodium bisulfate solution, 1 M aqueous sodium hydroxide solution, and brine, dried over magnesium sulfate, and concentrated to give a white solid. The unpurified compound was dissolved in 40 mL of ethyl acetate and allowed to stir over 20% palladium hydroxide on carbon under an atmosphere of hydrogen overnight. The reaction mixture was then filtered through a pad of Celite and concentrated. The resultant phenol was dissolved in 40 mL of DMF and added dropwise over a 30-min period via cannula to a mixture of 2.60 g (65.0 mmol) of sodium hydride (60% dispersion in mineral oil) at 0° C. A 10-mL portion of DMF was added. After the mixture was allowed to stir at 0° C. for 30 min, a solution of 14.3 g (55.0 mmol) of (2S)-glycidyl 3-nitrobenzene sulfonate in 40 mL of DMF was added dropwise over a 20-min period. After the reaction was judged to be complete by TLC analysis, it was quenched with water, diluted with ethyl acetate, washed sequentially with water, 1 M aqueous sodium hydroxide solution, and brine, dried over magnesium sulfate, and concentrated. Purification by flash chromatography (silica gel, 10% ethyl acetate/hexane) gave 5.04 g (36% overall yield) of the title compound: $^1$H NMR (400 MHz, CD$_3$OD) δ6.82 (d, 2H, J=9.1 Hz), 6.74 (d, 2H, J=9.1 Hz), 4.22 (dd, 1 H, J=2.6, 11.2 Hz), 3.79 (dd, 1H, J=6.2, 11.2 Hz), 3.30 (m, 1H), 2.84 (t, 1 H, J=4.6 Hz), 2.71 (dd, 1H, J=2.7, 5.0 Hz), 0.97 (s, 9H), 0.15 (s, 6H).

EXAMPLE 3

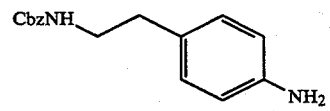

2-(4-Aminophenyl)ethylcarbamic acid phenylmethyl ester

A solution of 5.00 g (36.7 mmol) of 2-(4-aminophenyl)ethylamine in 100 mL of chloroform was cooled to 0° C. and 3.72 g (5.20 mL, 36.8 mmol) of triethylamine was added. A solution of 6.26 g (5.2 mL, 36.8 mmol) of benzyl chloroformate in 40 mL of chloroform was then added dropwise over a 30-min period. The reaction was allowed to stir at 0° C. for 2 h. It was diluted with 100 mL of chloroform, washed with 100-mL portions of water and brine, dried over sodium sulfate and concentrated. The residue was dissolved in 50% ethyl acetate/hexane and stirred with 30 g of silica gel, filtered, and concentrated. Further purification by recrystallization from ethyl acetate/hexanes gave 4.82 g (49%) of the title compound as a white solid: $^1$H NMR (400 MHz, CDCl$_3$) 7.33 (s, 5H), 6.94 (d, 2H, J=8.2 Hz), 6.60 (d, 2H, J=8.2 Hz), 5.07 (s, 2H), 4.84 (broad s, 1H), 3.55 (broad s, 2H), 3.37 (m, 2H), 2.67 (t, 2H, J=6.9 Hz). FAB MS m/z 271 (M+1).

EXAMPLE 4

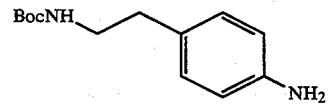

2-(4-Aminophenyl)ethylcarbamic acid 1,1-dimethylethyl ester

A solution of 817 mg (6.00 mmol) of 2-(4-aminophenyl)ethylamine in 20 mL of tetrahydrofuran was treated with 1310 mg (6.00 mmol) of di-tert-butyl dicarbonate. After the reaction mixture was stirred at room temperature for 0.5 h, it was concentrated. Trituration from a solution of 5 mL of ether and 20 mL of hexane gave 1.04 g (73%) of the title compound as a pale yellow solid: $^1$H NMR (400 MHz, CDCl$_3$) 6.94 (d, 2H, J=8.2 Hz), 6.59 (d, 2H, J=8.2 Hz), 4.51 (broad s, 1H), 3.58 (broad s, 2H), 3.27 (m, 2H), 2.63 (t, 2H, J=7.0 Hz), 1.38 (s, 9H). FAB MS m/z 237 (M+1).

EXAMPLE 5

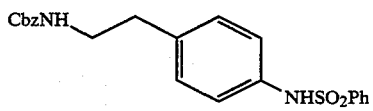

N-[4-[2-[(phenylmethoxycarbonyl)amino]ethyl]-phenyl]benzenesulfonamide

A solution of 868 mg (3.22. mmol) of Cbz amine from Example 3 in 15 mL of dichloromethane was cooled to 0° C. and treated with 0.286 mL (3.54 mmol) of pyridine followed by 569 mg (0.41 mL, 3.22 mmol) of benzenesulfonyl chloride. The reaction mixture was stirred at room temperature for 2 h and then partitioned between chloroform and water. The organic phase was washed sequentially with 5% aqueous hydrochloric acid and saturated aqueous sodium bicarbonate, dried over magnesium sulfate, and concentrated. Purification by recrystallization from ethyl acetate/hexane gave 630 mg (48%) of the title compound as a white solid: $^1$H NMR (400 MHz, CDCl$_3$) 7.72 (d, 2H, J=7.2 Hz), 7.48 (m, 1H), 7.39 (m, 2H), 7.33 (m, 5H), 7.02 (d, 2H, J=8.3 Hz), 6.95 (d, 2H, J=8.3 Hz), 6.55 (s, 1H), 5.06 (s, 2H), 4.68 (broad s, 1H), 3.37 (m, 2H), 2.72 (t, 2H, J=6.9 Hz). FAB MS m/z 411 (M+1).

EXAMPLE 6

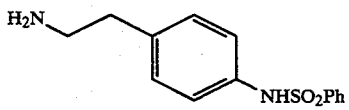

N-[4-(2-aminoethyl)phenyl]benzenesulfonamide

A solution of 600 mg (1.46 mmol) of Cbz amine from Example 5 in 18 mL of methanol was stirred over 20% palladium hydroxide on carbon under an atmosphere of hydrogen for 2.5 h. The reaction mixture was filtered through a Celite pad and concentrated to give 360 mg (89%) of a white solid: $^1$H NMR (400 MHz, CD$_3$OD) δ7.73 (d, 2H, J=7.1 Hz), 7.52 (t, 1H, J=7.4 Hz), 7.44 (t, 2H, J=7.5 Hz), 7.04 (d, 2H, J=8.7 Hz), 6.99 (d, 2H, J=8.6 Hz), 2.82 (t, 2H, J=7.3 Hz), 2.66 (t, 2H, J=7.3 Hz).

EXAMPLE 7

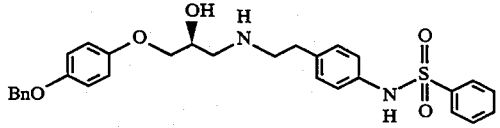

(S)-N-[4-[2-[[2-hydroxy-3-[(4-phenylmethoxy)phenoxy]propyl]amino]ethyl]phenylbenzenesulfonamide A solution of 406 mg (1.47 mmol) of amine from Example 6 in 8 mL of anhydrous methanol was treated with 280 mg (1.10 mmol) of epoxide from Example 1. The solution was heated at reflux under nitrogen overnight, then cooled to room temperature and concentrated. Purification by flash chromatography (silica gel, 5:4:1 ethyl acetate:hexane: 10% methanolic ammonium hydroxide) gave 282 mg (48%) of the title compound: $^1$H NMR (400 MHz, CD$_3$OD) δ7.71 (d, 2H), 7.52 (m, 1H), 7.1–7.4 (7H), 7.06 (d, 2H), 7.00 (d, 2H), 6.75 (d, 2H), 6.70 (d, 2H), 5.02 (s, 2H), 3.99 (m, 1H), 3.82 (d, 2H), 2.6–2.9 (m, 6H).

EXAMPLE 8

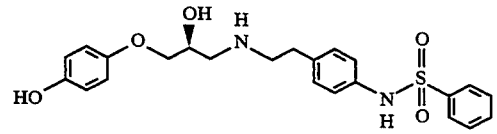

(S)-N-[4-[2-[[2-hydroxy-3-(4-hydroxyphenoxy)propyl]amino]ethyl]phenyl]benzenesulfonamide A solution of 282 mg (0.529 mmol) of benzyl ether from Example 7 in 5 mL of methanol and 5 mL of tetrahydrofuran was treated with 100 mg of 20% palladium hydroxide on carbon under an atmosphere of hydrogen for 2 h. It was then filtered and concentrated. Purification by flash chromatography (silica gel, 5:4:2 ethyl acetate:hexane:10% methanolic ammonium hydroxide) gave 141 mg (60%) of the title compound as a foam: $^1$H NMR (400 MHz, CD$_3$OD) 7.71 (d, 2H, J=7.1 Hz), 7.52 (m, 1H), 7.43 (m, 2H), 7.07 (d, 2H, J=8.5 Hz), 6.99 (d, 2H, J=8.5 Hz), 6.75 (d, 2H, J=9.1), 6.68 (d, 2H, J=9.1 Hz), 3.98 (m, 1H), 3.82 (d, 2H, J=5.4 Hz), 2.6–2.9 (m, 6H). FAB MS m/z 443 (M+1).

EXAMPLE 9

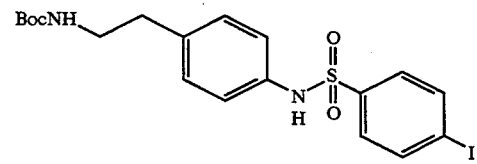

N-[4-[2-[[(1,1-dimethylethoxy)carbonyl]amino]ethyl]-phenyl]-4-iodobenzenesulfonamide In a manner analogous to that of Example 5, the title compound was prepared from the Boc amine in Example 2 and 4iodobenzenesulfonyl chloride: $^1$H NMR (400 MHz, CD$_3$OD) a 7.86 (d, H), 7.46 (d, 2H), 7.07 (d, 2H), 6.99 (d, 2H), 3.27 (t, 2H), 2.76 (t, 2H), 1.38 (s, 9H).

EXAMPLE 10

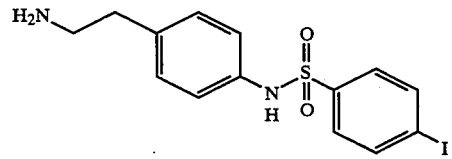

N-[4-(2-aminoethyl)phenyl-4-iodobenzenesulfonamide

A solution of 1.80 g of Boc amine from Example 9 in 1:1 trifluoroacetic acid:dichloromethane was allowed to stand at room temperature for 15 min at which time TLC analysis indicated the reaction was complete. The solution was then concentrated. Purification by flash chromatography (silica gel, 15% of 10:1 methanol:concentrated ammonium hydroxide in dichloromethane) gave the title compound as a crystalline solid: $^1$H NMR (200 MHz, CD₃OD) δ7.80 (d, 2H), 7.46 (d, 2H), 7.06 (d, 2H), 6.98 (d, 2H), 2.81 (t, 2H), 2.65 (t, 2H).

EXAMPLE 11

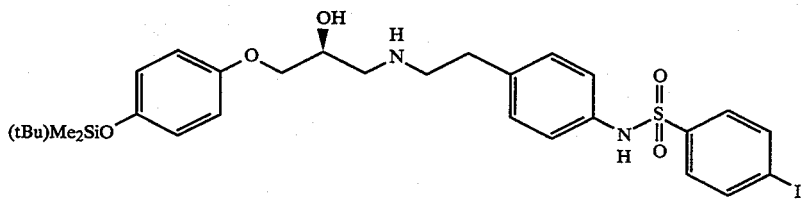

(S)-N-[4-[2-[[2-hydroxy-3-[[4-[[(1,1-dimethylethyl)-dimethylsilyl]oxy]phenoxylpropyl]amino]ethyl]phenyl]-4-iodo-benzenesulfonamide In a manner analogous to that of Example 7, the title compound was prepared from the epoxide from Example 2 and the amine from Example 10: ¹H NMR (400MHz, CD₃OD) δ7.82 (d, 2H, J = 8.6 Hz), 7.43 (d, 2H, 8.6 Hz), 7.10 (d, 2H, J=8.5 Hz), 6.79 (d, 2H), 6.73 (d, 2H), 4.01 (m, 1H), 3.87 (d, 2H), 3.91-2.69 (m, 6H), 0.96 (s, 9H), 0.15 (s, 6H).

EXAMPLE 12

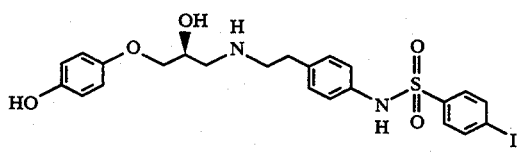

(S)-N-[4-[2-[[2-hydroxy-3-(4-hydroxyphenoxy)propyl-]amino]ethyl]phenyl]-4-iodobenzenesulfonamide A 182-mg (0.266 mmol) sample of silyl ether from Example 11 was treated with 3% methanolic hydrogen chloride (prepared by adding 1 mL of acetyl chloride to 19 mL of methanol at 0° C.). After the solution was allowed to stir at room temperature for 1h, it was concentrated. Purification by flash chromatography (silica gel, 10% of 10:1 methanol:concentrated ammonium hydroxide in dichloromethane) gave 106 mg (70%) of the title compound: ¹H NMR (400MHz, CD₃OD) δ7.82 (d, 2H, J=8.6 Hz), 7.43 (d, 2H, 8.6 Hz), 7.10 (d, 2H, J=8.5 Hz), 6.99 (d, 2H, J=8.5 Hz), 6.74 (d, 2H, J=9.0 Hz), 6.68 (d, 2H, J=9.0 Hz), 4.00 (m, 1H), 3.83 (d, 2H, J=5.5 Hz), 3.34-2.67 (m, 6H); FAB MS m/z 569 (M+1), 309, 154.

EXAMPLE 13

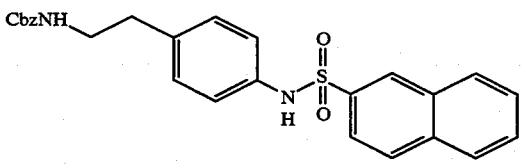

N-[4-[2-[(phenylmethoxycarbonyl)amino]ethyl]-phenyl]-2-naphthalenesulfonamide

In a manner analogous to that of Example 5, the title compound was prepared from the Cbz amine from Example 3 and 2-naphthalenesulfonyl chloride: ¹H NMR (400 MHz, CDCl₃) δ8.32 (s, 1H), 7.85 (m, 3H), 7.71 (dd, 1H, J=1.8, 8.7 Hz), 7.61-7.52 (m, 2H), 7.34-7.28 (m, 5H), 6.99 (s, 4H), 6.77 (br s, 1H), 5.04 (s, 2H), 4.65 (br s, 1H), 3.33 (br q, 2H, J=5.9 Hz), 2.68 (t, 2H, J=7.0 Hz); FAB MS m/z 461 (M+1), 270.

EXAMPLE 14

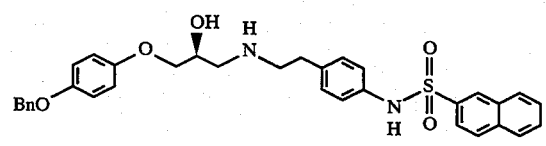

(S)-N-[4-[2-[[2-hydroxy-3-[(4-phenylmethoxy)phenoxy]propyl]amino]ethyl]phenyl]-2-naphthalenesulfonamide The Cbz amine from Example 13 was deprotected as described in Example 6. In a manner analogous to that of Example 7, the title compound was prepared from the resultant amine and the epoxide from Example 1: ¹H NMR (400 MHz, CD₃OD) δ8.27 (s, 1H), 7.93-7.87 (m, 3H), 7.71 (dd, 1H, J=1.9, 8.7 Hz), 7.62-7.54 (m, 2H), 7.39 (d, 2H, J=7.2 Hz), 7.34 (t, 2H, J=7.3 Hz), 7.27 (t, 1H, J=7.1 Hz), 7.04 (d, 2H, J=9.0 Hz), 7.01 (d, 2H, J=9.0 Hz), 6.88 (d, 2H, J=9.1 Hz), 6.79 (d, 2H, J=9.1 Hz), 4.99 (s, 2H), 3.96 (m, 1H), 3.82 (d, H, J=5.3 Hz), 2.80-2.63 (m, 6H); FAB MS m/z 583 (M+1).

EXAMPLE 15

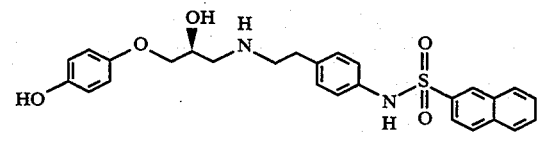

(S)-N-[4-[2-[[2-hydroxy-3-(4-hydroxyphenoxy)propyl-]amino]ethyl]phenyl]-2-naphthalenesulfonamide In a manner analogous to that of Example 8, the title compound was prepared from the benzyl ether from Example 14: ¹H NMR (400 MHz, CD₃OD) δ8.28 (s, 1H), 7.95-7.89 (m, 3H), 7.72 (dd, 1, H, J=1.9, 8.7 Hz), 7.62-7.57 (m, 2H), 7.07-7.01 (m, 4H), 6.73 (d, 2H, J=9.0 Hz), 6.67 (d, 2H, J=9.0 Hz), 3.97 (m, 1H), 3.81 (d, 2H, J=5.2 Hz), 2.85-2.68 (m, 6H); FAB MS m/z 493 (M+1).

EXAMPLE 16

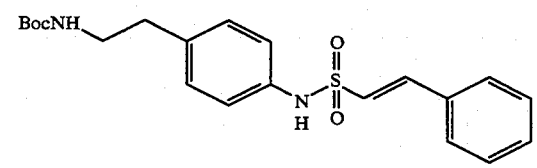

N-[4-[2-[[(1,1-dimethylethoxy)carbonyl]amino]ethyl]-phenyl]-β-styrenesulfonamide In a manner analogous to that of Example 5, the title compound was prepared from the Boc amine from Example 17: ¹H NMR (400 MHz, CD₃OD) δ7.25–7.12 (m, 7H), 7.11 (d, 2H, J=6.8 Hz), 3.26 (m, 2H), 3.03 (m, 2H), 2.86 (t, 2H, J=7.4 Hz), 2.72 (t, 2H, J=7.4 Hz).

EXAMPLE 19

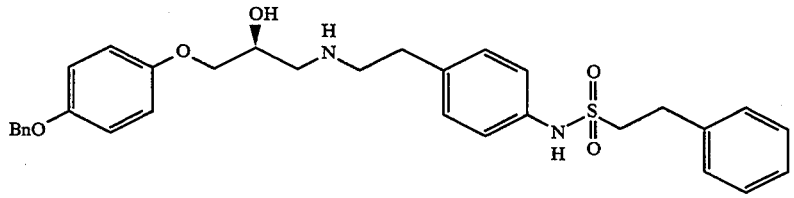

ample 4 and β-styrenesulfonyl chloride: ¹H NMR (400 MHz, CDCl₃) δ7.47 (d, 1H, J =15.4 Hz), 7.42–7.33 (m, 5H), 7.11 (s, 4H), 6.77 (d, 1H, J=15.4 Hz), 6.56 (br s, 1H), 4.48 (br s, 1H), 4.10 (br m, 2H), 2.72 (t, 2H, J=7.1 Hz), 1.39 (s, 9H).

EXAMPLE 17

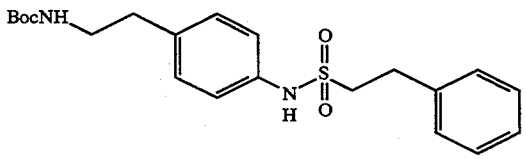

(S)-N-[4-[2-[[2-hydroxy-3-[(4-phenylmethoxy)phenoxy]propyl]amino]ethyl]phenyl]-2-phenylethanesulfonamide.

In a manner analogous to that of Example 7, the title compound was prepared from the amine from Example 18 and the epoxide from Example 1: ¹H NMR (400 MHz, CD₃OD) δ7.40–7.09 (m, 14H), 6.88 (d, 2H, J=9.2 Hz), 6.81 (d, 2H, J=9.2 Hz), 4.00 (m, 1H), 3.85 (d, 2H, J=5.3 Hz), 3.25 (m, 1H), 3.02 (m, 1H), 2.91–2.78 (m, 5H), 2.72 (dd, 1H, J=8.1, 12.2 Hz); FAB MS m/z 561 (M+1).

EXAMPLE 20

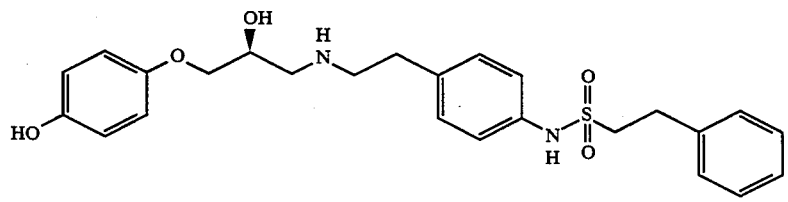

N-[4-[2-[[(1,1-dimethylethoxy)carbonyl]amino]ethyl]-phenyl]-2-phenylethanesulfonamide A solution of 204 mg (0.507 mmol) of Boc amine from Example 16 in methanol was stirred over 20% palladium hydroxide under an atmosphere of hydrogen overnight. The reaction mixture was then filtered and concentrated. Purification by flash chromatography (silica gel, 30% ethyl acetate/hexane) gave 168 mg (82%) of the title compound as a white solid: ¹H NMR (200 MHz, CDCl₃) δ7.39–7.21 (m, 3H), 7.15–7.06 (m, 4H), 6.96 (d, 2H, J=8.1 Hz), 6.25 (s, 1H), 4.49 (br s, 1H), 3.35–3.24 (m, 4H), 3.18–3.05 (m, 2H), 2.72 (t, 2H, J=7.1 Hz), 1.40 (s, 9H).

EXAMPLE 18

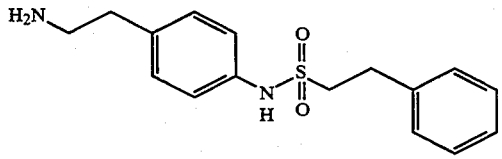

N-[4-(2-aminoethyl)phenyl]-2-phenylethanesulfonamide

In a manner analogous to that of Example 10, the title compound was prepared from the Boc amine from Ex- (S)-N-[4-[2-[[2-hydroxy-3-(4-hydroxyphenoxy)propyl]amino]ethyl]-phenyl]-2-phenylethanesulfonamide In a manner analogous to that of Example 8, the title compound was prepared from the benzyl ether from Example 19: ¹H NMR (400 MHz, CD₃OD) δ7.25–7.15 (m, 7H), 7.11 (d, 2H, J=7.0 Hz), 6.75 (d, 2H, J=9.1 Hz), 6.68 (d, 2H, J=9.1 Hz), 4.05 (m, 1H), 3.89–3.83 (overlapping dd, 2H), 3.26 (m, 1H), 3.05–2.95 (m, 4H), 2.88–2.82 (m, 3H); FAB MS m/z 471 (M+1).

EXAMPLE 21

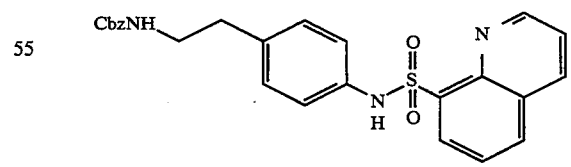

N-[4-[2-[(phenylmethoxycarbonyl)amino]ethyl]-phenyl]-8-quinolinesulfonamide

In a manner analogous to that of Example 5, the title compound was prepared from the Cbz amine from Example 3 and 8quinolinesulfonyl chloride: ¹H NMR (400 MHz, d₆-DMSO) 9.94 (s, H), 9.12 (m, 1H), 8.49 (dd, 1H), 8.31 (dd, 1H), 8.24 (dd, 1H), 7.70 (m, 2H), 7.2–7.4

(m, 4H), 6.94 (d, 2H), 6.88 (d, 2H), 4.94 (s, 2H), 3.04 (m, 2H), 2.48 (t, 2H). FAB MS m/z 462 (M+1).

EXAMPLE 22

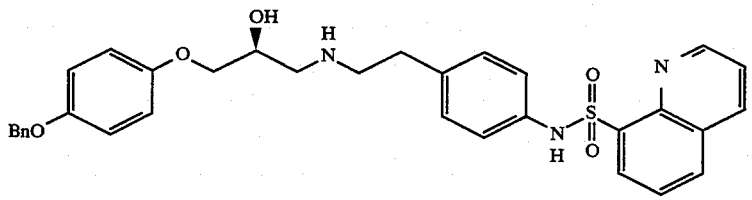

(S)-N-[4-[2-[[2-hydroxy-3-[(4-phenylmethoxy)phenoxy]propyl]amino]-ethyl]phenyl]-8-quinolinesulfonamide The Cbz amine from Example 21 was deprotected as described in Example 6. In a manner analogous to that of Example 7, the title compound was prepared from the resultant amine and the epoxide from Example 1: $^1$H NMR (400 MHz, CD$_3$OD) δ9.12 (m, 1H), 8.49 (d, 1H), 8.31 (dd, 1H), 8.24 (dd, 1H), 7.3–7.5 (m, 7H), 7.07 (d, H, J=8.5 Hz), 6.99 (d, 2H, J=8.5 Hz), 6.75 (d, 2H, J=9.1 ), 6.68 (d, H, J=9.1 Hz), 5.04 (s, 2H), 3.98 (m, 1H), 3.82 (d, 2H, J=5.4 Hz), 2.5–2.9 (m, 6H). FAB MS m/z 584 (M+1).

EXAMPLE 23

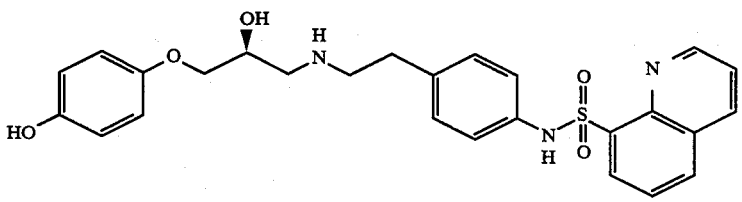

(S)-N-[4-[2-[[2-hydroxy-3-(4-hydroxyphenoxy)propyl]amino]ethyl]phenyl]-8-quinolinesulfonamide In a manner analogous to that of Example 8, the title compound was prepared from the benzyl ether from Example 22: $^1$H NMR (400 MHz, CD$_3$OD) 9.95 (s, 1H), 9.12 (m, 1H), 8.48 (d, 1H, J=6.9 Hz), 8.30 (d, 1H, J=6.9 Hz), 8.24 (d, 1H, J=7.0 Hz), 7.52 (m, H), 7.07 (d, 2H, J=8.6 Hz), 6.99 (d, 2H, J=8.6 Hz), 6.75 (d, 2H, J=9.1 Hz), 6.68 (d, 2H, J=9.1 Hz), 3.98 (m, 1H), 3.82 (d, 2H, J=5.4 Hz), 3.34 (s, 1H), 2.6–2.9 (m, 6H). FAB MS m/z 494 (M+1).

EXAMPLE 24

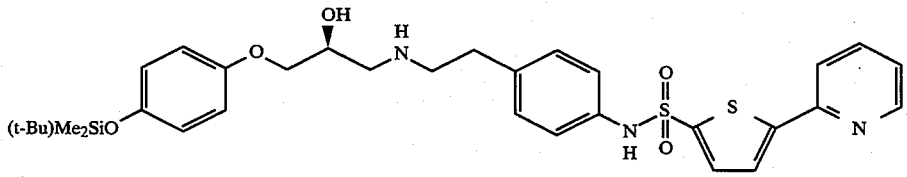

N-[4-[2-[[(1,1-dimethylethoxy)carbonyl]amino]ethyl]-phenyl]-5-(pyridinyl)-2-thiophenesulfonamide In a manner analogous to that of Example 5, the title compound was prepared from the Boc amine from Example 4 and 5-(pyridin-2-yl)-2-thiophenesulfonyl chloride: $^1$H NMR (400 MHz, CD$_3$OD) 8.48 (d, 1, H, J=5.2 Hz), 7.81 (m, 2H), 7.54 (d, 1H, J=4.1 Hz), 7.41 (m, 1H), 7.30 (m, 1H), 7.11 (s, 4H), 3.18 (t, 2H, J=7.1 Hz), 2.67 (t, 2H, J=7.1 Hz), 1.38 (s, 9H). FAB MS m/z 460 (M+1).

EXAMPLE 25

(S)-N-[4-[2-[[2-hydroxy-3-[[4-[[(1,1-dimethylethyl)dimethylsilyl]oxy]phenoxy]propyl]amino]ethyl]phenyl]-5-(pyridin-2-yl)-2-thiophene]sulfonamide The Boc amine from Example 24 was deprotected as described in Example 10. In a manner analogous to that of Example 7, the title compound was prepared from the resultant amine and the epoxide from Example 2: $^1$H NMR (400 MHz, CD$_3$OD) 8.48 (d, 1 H, J =5.1 Hz), 7.80 (m, 2H), 7.54 (d, 1H, J=4.1 Hz), 7.39 (d, 1H, J=4.1 Hz), 7.30 (m, 1H), 7.15 (d, 2H, J=8.7 Hz), 7.10 (d, 2H, J=8.8 Hz), 6.74 (d, 2H, J=9.0 Hz), 6.67 (d, 2H, J=9.0 Hz), 3.99 (m, 1H), 3.82 (d, 2H, J=5.4 Hz), 2.7–2.9 (m, 6H), 1.01 (s, 9H), 0.15 (s, 6H).

EXAMPLE 26

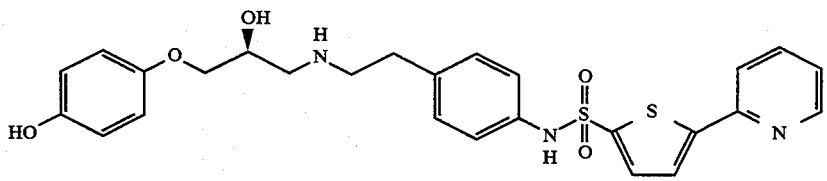

(S)-N-[4-[2-[[2-hydroxy-3-(4-hydroxyphenoxy)propyl]amino]ethyl]phenyl]-5-[2-(pyridin-2-yl)thiophenelsulfonamide In a manner analogous to that of Example 12, the title compound was prepared from the silyl ether from Example 25: $^1$H NMR (400 MHz, CD$_3$OD) 8.48 (m, 1H), 7.80 (m, 2H), 7.54 (d, 1H, J=4.0 Hz), 7.40 (d, 1H, J=4.0 Hz), 7.29 (m, 1H), 7.13 (d, 2H, J=8.8 Hz), 7.10 (d, 2H, J=8.8 Hz), 6.74 (d, 2H, J=9.1 Hz), 6.68 (d, 2H, J= 9.1 Hz), 3.99 (m, 1H), 3.83 (d, 2H, J=5.4 Hz), 2.7–2.9 (m, 6H). FAB MS m/z 526 (M+1).

EXAMPLE 27

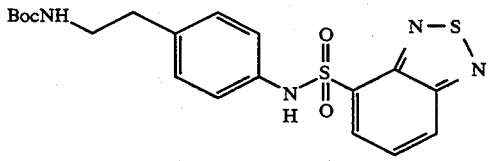

N-[4-[2-[[(1,1-dimethylethoxy)carbonyl]amino]ethyl]phenyl]-4-(benzo-2,1,3-thiadiazole)sulfonamide In a manner analogous to that of Example 5, the title compound was prepared from the Boc amine from Example 4 and benzo-2,1,3-thiadiazole-4-sulfonyl chloride: $^1$H NMR (400 MHz, CDCl$_3$) 8.23 (m, 2H), 7.71 (dd, 1H, J=7.1, 8.7 Hz), 7.04 (m, 4H), 3.16 (m, 2H), 2.65 (t, 2H, J=7.0 Hz), 1.37 (s, 9H). FAB MS m/z 435 (M+1).

EXAMPLE 28

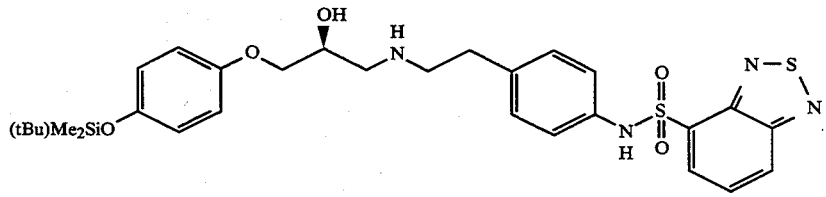

(S)-N-[4-[2-[[2-hydroxy-3-[[4-[[(1,1-dimethylethyl)dimethylsilyl]oxy]phenoxy]propyl]amino]ethyl]phenyl]-4-(benzo-2,1,3-thiadiazole)sulfonamide The Boc amine from Example 27 was deprotected as described in Example 10. In a manner analogous to that of Example 7, the title compound was prepared from the resultant amine and the epoxide from Example 2: $^1$H NMR (400 MHz, CD$_3$OD) 8.15 (m, 2H), 7.69 (dd, 1H, J=7.2, 8.7 Hz), 6.97 (s, 4H), 6.73 (d, 2H, J=9.1 Hz), 6.69 (d, 2H, J=9.1 Hz), 4.88 (m, 1H), 3.80 (d, 2H, J=5.1 Hz), 2.6–2.85 (m, 6H), 0.99 (s, 9H), 0.14 (s, 6H).

EXAMPLE 29

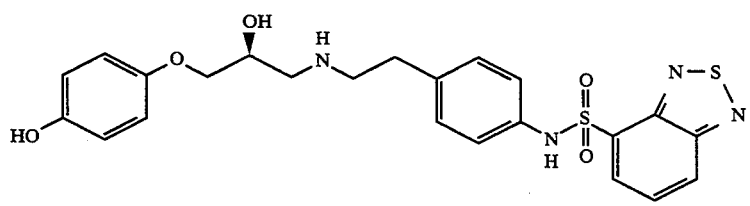

(S)-N-[4-[2-[[2-hydroxy-3-(4-hydroxyphenoxy)propyl]amino]ethyl]-phenyl]-4-(benzo-2,1,3-thiadiazole)sulfonamide In a manner analogous to that of Example 12, the title compound was prepared from the silyl ether from Example 28: $^1$H NMR (400 MHz, CD$_3$OD) 8.18 (m, 2H), 7.69 (dd, 1H, J=7.1, 8.7 Hz), 6.97 (s, 4H), 6.73 (d, 2H, J=9.1 Hz), 6.67 (d, 2H, J=9.1 Hz), 4.89 (m, 1H), 3.80 (d, 2H, J=5.0 Hz), 2.6–2.8 (m, 6H). FAB MS m/z (M+1), 309.

EXAMPLE 30

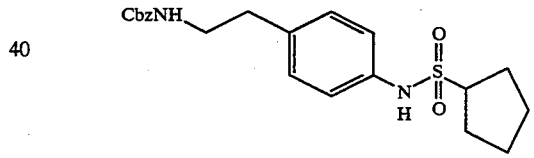

N-[4-[2-[(phenylmethoxycarbonyl)amino]ethyl]phenyl]cyclopentanesulfonamide

Cyclopentanesulfonyl chloride was prepared according to the procedure of S. N. Bhattacharya, et. al., J. Chem. Soc. (C), 1265–1267 as follows. To a solution of 2.7 g (1.6 mL, 20 mmol) of sulfuryl chloride in 5 mL of hexane at 0° C. was added a solution of 5 mL (10 mmol) of 2 M cyclopentylmagnesium chloride in ether over a 15-min period. The reaction mixture was allowed to warm to room temperature and stir overnight. The mixture was recooled to 0° C. and a 5-mL portion of ether was added followed by a 10-mL portion of water. The layers were separated and the organic phase was washed with water, dried over sodium sulfate and concentrated to give 1.12 (70%) of cyclopentanesulfonyl chloride. This compound was used without further purification to prepare the title compound from the Cbz amine from Example 3 in a manner analogous to that of Example 5: $^1$H NMR (400 MHz, CDCl$_3$) δ7.34–7.30 (m, 5H), 7.13 (s, 4H), 6.44 (br s, 1H), 5.07 (s, 2H), 4.74 (br, s, 1H), 3.50–3.39 (m, 3H), 2.76 (br t, 2H), 2.09–1.91 (m, 4H), 1.86–1.76 (m, 2H), 1.64–1.54 (m, 2H); FAB MS m/z 403 (M+1).

EXAMPLE 31

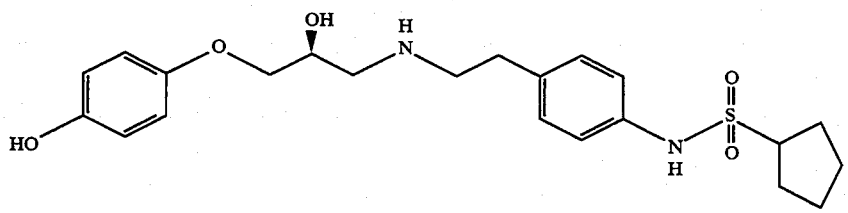

(S)-N-[4-[2-[[2-hydroxy-3-(4-hydroxyphenoxy)propyl]amino]ethyl]phenyl]cyclopentanesulfonamide Following the procedures outlined in Examples 6, 7, and 8, the title compound was prepared from the Cbz amine from Example 30: $^1$H NMR (400 MHz, CD$_3$OD) δ7.19 (s, 4H), 6.75 (d, 2H, J=9.1 Hz), 6.68 (d, 2H, J=9.0 Hz), 4.02 (m, 1H), 3.85 (d, 2H, J=5.3 Hz), 3.49 (m, 1H), 2.95–2.73 (m, 6H), 2.03–1.86 (m, 4H), 1.79–1.71 (m, 2H), 1.64–1.53 (m, 2H); FAB MS m/z 435 (M+1).

EXAMPLE 32

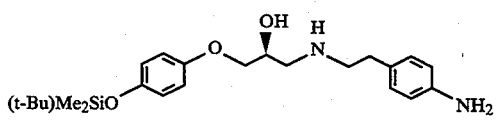

(S)-N-[2-[4-(aminophenyl)]ethyl]-2-hydroxy-3-[4-[[(1,1-Dimethylethyl)dimethylsilyl]oxy]phenoxy]propylamine In a manner analogous to that of Example 7, the title compound was prepared from the epoxide from Example 2 and 2-(4-aminophenyl)ethylamine. Purification by flash chromatography (silica gel, 10% methanol:dichloromethane) gave the title compound: $^1$H NMR (400 MHz, CDCl$_3$) δ6.97 (d, 2H), 6.72 (s, 4H), 6.61 (d, 2H), 3.98 (m, 1H), 3.87 (d, 2H), 3.55 (br s, 1H), 2.91–2.66 (m, 6H), 2.00 (br s, 3H), 0.93 (s, 9H), 0.14 (s, 6H).

EXAMPLE 33

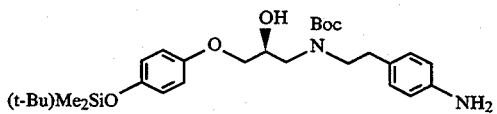

(S)-N-[2-[4-(aminophenyl)]ethyl]-2-hydroxy-3-[4-[[( 1,1-Dimethylethyl)dimethylsilyl]oxy]phenoxy]propylcarbamic acid 1,1-dimethylethyl ester To a solution of 2.14 g (1.12 mmol) of amine from Example 32 in 50 mL of THF at 0° C. was added a solution of di-tertbutyldicarbonate in 10 mL of THF. The reaction mixture was stirred at 0° C. for 4.5 h, then concentrated. Purification by flash chromatography (silica gel, 40% ethyl acetate:hexanes) gave 2.23 g (84%) of the title compound as an oil: $^1$H NMR (400 MHz, CDCl$_3$) δ7.00–6.90 (br m, 2H), 6.73 (s, 4H), 6.61 (d, 2H, J=8.3 Hz), 4.06 (br m, 1H), 4.90–4.75 (br m, 2H), 3.44–3.28 (br m, 4H), 2.69 (m, 2H), 1.43 (s, 9H), 0.95 (s, 9H), 0.14 (s, 6H).

EXAMPLE 34

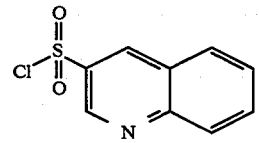

3-Quinolinesulfonyl chloride

A solution of n-butyllithium (20 mL of 2.5 M in hexanes, 50 mmol) in 250 mL of anhydrous ether was cooled in a dry ice-acetone bath and treated over a 10 min period with a solution of 3-bromoquinoline (5.0 g, 24 mmol) in 50 mL of ether. The resulting slurry was stirred for 15 min at −78° C., and was then rapidly cannulated into a solution of sulfuryl chloride (7 mL, 100 mmol) in 500 mL of anhydrous ether cooled to −78° C. The resulting orange slurry was stirred at −78° C. for 30 min, and was then warmed to 0° C. over 30 min and concentrated under reduced pressure to a thick semisolid yellow mass, which was partitioned between water and ethyl acetate. After addition of sodium bicarbonate, the aqueous layer was removed and extracted with an additional 50 mL of ethyl acetate. The combined organic extracts were dried over sodium sulfate and concentrated to a yellow oil. Flash chromatography (5%, then 25% EtOAc-hexanes eluant) afforded ca. 2 g of a yellow oil, which crystallized upon standing. Trituration with hexanes gave 250 mg of title compound as a white solid. NMR (400 MHz, d-6 DMSO) 9.42 (d, 1H, J=2.0 Hz), 9.32 (s, 1H), 8.45 (d, 1H, J=8.1 Hz), 8.28 (d, 1H, J=8.8 Hz), 8.11 (apparent t, 1H), 7.94 (apparent t, 1H).

EXAMPLE 35

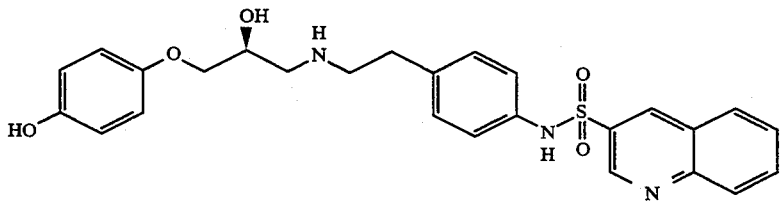

(S)-N-[4-[2-[[2-hydroxy-3-(4-hydroxyphenoxy)propyl-]amino]ethyl]phenyl]-3-quinolinesulfonamide To a solution of the TBS-protected aniline from Example 33 (260 mg, 0.50 mmol) and pyridine (50 µL, 0.60 mmol) in 4 mL of methylene chloride was added 3-quinolinesulfonyl chloride (118 mg, 0.52 mmol). The red solution was stirred at room temperature for one hour and was concentrated under reduced pressure. The residue was dissolved in 2 mL of methanol, and approximately 5 mL of a 3% solution of HCl in methanol was added. After stirring at room temperature for 2 h, the solution was concentrated, and the residue was dissolved in 5 mL of 10% methanolic ammonium hydroxide. After removal of solvent in vacuo, the residue was applied directly to a silica gel column. Elution with 5:4:1 EtOAc:hexanes:10% methanolic NH4OH afforded 186 mg (0.38 mmol, 76% yield) of the title compound as an off-white solid. NMR (400 MHz, CD3OD) 9.02 (d, 1H, J=2.1 Hz), 8.67 (d, 1H, J=2.1 Hz), 8.03 (d, 1H, J=8.6 Hz), 7.97 (d, 1H, J=7.9 Hz), 7.86 (apparent t, 1H), 7.66 (apparent t, 1H), 7.04 (two overlapping d, 4H), 6.72 (d, 2H, J=9.1 Hz), 6.67 (d, 2H, J=9.1 Hz), 3.98 (m, 1H), 3.81 (d, 2H, J=5.4 Hz), 2.84 (m, 3H), 2.72 (m, 3H). FAB MS m/z 494 (M+1).

EXAMPLE 36 magnesium sulphate, concentrated, dissolved in methanol (20 ml), and treated with 20% palladium hydroxide on carbon 350 mg, under an atmosphere of hydrogen for 16h. The reaction was diluted with methanol (60 ml), filtered, concentrated, and purified by flash chromatography (silica gel, 2% methanol/dichloromethane), to give the amine 888 mg (68%).

To amine, prepared above, 60.5 mg (0.09 mmol) and pyridine 0.016 mL (0.2 mmol) in dichloromethane (0.5 ml) at 0° C., was added a solution of monomethyl adipyl chloride (0.1 mmol, prepared from monomethyl adipate 0.015 mL (0.1 mmol), oxalyl chloride 0.050 mL (2M solution in dichloromethane, 0.1 mmol), and DMF (1 drop) in dichloromethane at 0° C. for 30rain). After 1 h the reaction was diluted with dichloromethane (10 ml), work up as above and purification by flash chromatography, using the same solvent system as above, yielded the desired amide 67 mg. The material was dissolved in THF (1 ml) and treated with tetrabutylammonium fluoride 0.088 mL (1M in THF, 0.088 mmol). After stirring for 2h, the solution was diluted with EtOAc (10 ml), washed with water (10ml), back extracted with EtOAc (2×5 ml), washed with brine (10ml), dried with anhydrous magnesium sulphate, concentrated and purified by flash chromatography (silica gel, 5% methanol/dichloromethane) to give the phenol 50 mg (70%).

A portion 11mg (0.0157 mmol) was treated with 1M

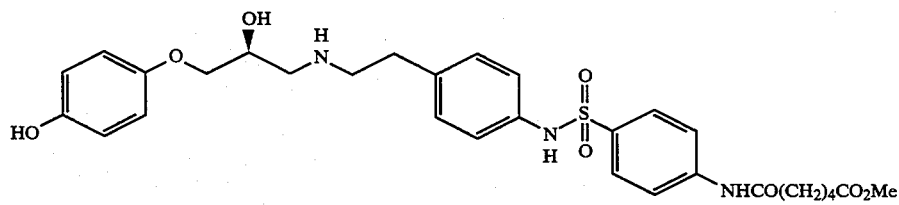

S(S)-N-[4-[2-[[2-hydroxy-3-(4-hydroxyphenoxy)propyl-]amino]ethyl]phenyl]-4-[(5-methoxycarbonyl)pentanoyl]amino]benzenesulfonamide Pyridine 0.314 mL (3.88 mmol) and 4-nitrobenzenesulfonyl chloride 454.3 mg (2.05 mmol) were added to a solution of BOC protected amine from Example 33 (lg, 1.94 mmol) in dichloromethane at 0° C. Stirring was continued for 2h, before diluting with EtOAc (40 ml), and washing with 3 M hydrochloric acid (2×10ml), saturated sodium bicarbonate solution (2×10ml), and brine (20 ml). The solution was dried over anhydrous hydrogen chloride in methanol (4.5 ml) at ambient temperature for 20 min, before concentration, and purification by preparative tlc (silica gel, 10% methanol (1% ammonium hydroxide)/dichloromethane)to give the title compound 5 mg (53%). $^1$H NMR (CD3OD) 7.66–7.62 (m, 4H), 7.08 (d, 2H, J=9.6 Hz), 7.01 (d, 2H, J=9.6 Hz), 6.74 (d, 2H, J=9.6Hz), 6.67(d, 2H, J=9.6Hz), 4.03–3.97(m, 1H), 3.84–3.82 (m, 2H), 3.63 (s,3H), 2.90–2.70 (m, 6H), 2.38–2.33 (m, 4H), and 1.72–1.60 (m,4H).

EXAMPLE 37

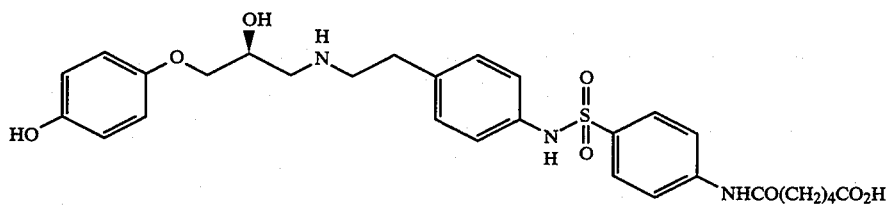

NHCO(CH2)4CO2H (S)-N-[4-[2-[[2-hydroxy-3-(4-hydroxyphenoxy)propyl]amino]ethyl]phenyl]-4-[(5-hydroxycarbonyl)pentanoyl]amino]benzenesulfonamide To the BOC protected phenolic methyl ester from Example 36 90 mg (0.129 mmol) in THF/water (2ml, 1/1) was added lithium hydroxide monohydrate 27 mg (0.645 mmol), stirring was continued for 16h, before the mixture was neutralised with 3M hydrochloric acid, concentrated, and purified by mplc (35 water (0.1% TFA)/65 methanol) to give the acid 86 mg. A portion 22 mg (0.032 mmol) was treated with trifluoroacetic acid/dichloromethane (1/1, 2 ml) at ambient temperature for 30min, before concentration, and purification by mplc (60 water (0.1% TFA)/40 methanol) to give the title compound 17 mg (90%). $^1$H NMR (CD$_3$OD) 7.67 (m, 4H), 7.18–7.05 (m, 4H), 6.80–6.68 (m, 4H), 4.21–4.14 (m, 1H), 3.98–3.85 (m, 2H), 3.27–3.10 (m, 4H), 2.95–2.89 (m, 2H), 2.42–2.28 (m, 4H), and 1.73–1.60 (m, 4H).

EXAMPLE 38

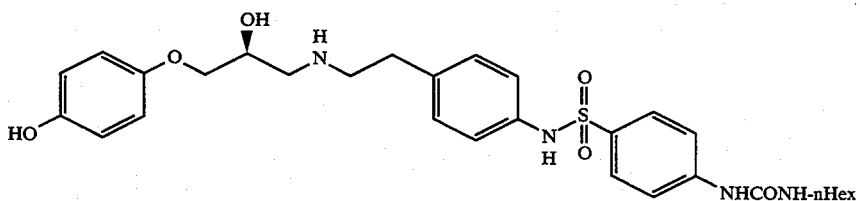

NHCONH-nHex (S)-N-[4-[2-[[2-hydroxy-3-(4-hydroxyphenoxy)propyl]amino]ethyl]phenyl]-4-(hexylaminocarbonylamino)-benzenesulfonamide To a suspension of 4-chlorosulphonylbenzene isocyanate 50 mg (0.23 mmol) at −40° C. in chloroform (0.5 ml), was added hexylamine 0.23 ml (1M solution in chloroform, 0.23 mmol). Stirring was continued with warming to ambient temperature for 16h, then the mixture was cooled to 0° C. and a solution of BOC protected amine from Example 33 (100 mg, 0.193 mmol) in dichloromethane (1 mL), containing pyridine 0.032 mL (0.4 mmol), was added. After 3h the solution was diluted with EtOAc (10 ml), washed with water (10ml), back extracted with EtOAc (2×5 ml), washed with brine (10ml), dried with anhydrous magnesium sulphate, concentrated, and purified by preparative tlc (silica gel, 2%methanol/dichloromethane) to give the urea 80 mg. This was treated with 1M hydrogen chloride in methanol (4.5 ml) at ambient temperature for 20min, before concentration and purification by preparative tlc (silica gel, 15% methanol (1% is ammonium hydroxide)/dichloromethane) to give the title compound 53.6 mg (47%). $^1$H NMR (CD$_3$OD) 7.58 (d, 2H, J=8Hz), 7.42 (d, 2H, J=8Hz), 7.09 (d, 2H, J=8Hz), 7.01 (d, 2H, J=8Hz), 6.78–6.65 (m, 4H), 4.06–4.00(m, 1H), 3.89–3.80 (m, 2H), 3.15 (t, 2H, J=7.2Hz), 2.87–265 (m, 6H), 1.53–1.46 (m, 2H), 1.40–1.27 (m, 6H), 0.92–0.88 (m, 3H).

Following the procedures outlined for Examples 1–38, the compounds listed in Tables 1 and 2 were prepared.

TABLE 1

| Example | R | Selected $^1$H NMR (CD$_3$OD) Data |
|---|---|---|
| 39 | 4-Me | 2.34(s, 3H) |
| 40 | 4-OMe | 3.79(s, 3H) |
| 41 | 4-Et | 2.65(q, 2H, J=7.7Hz), 1.19(t, 3H, J=7.7Hz) |
| 42 | 4-n-propyl | 2.60(t, 2H, J=7.6Hz), 1.60(hex, 2H, J=7.5Hz), 0.89(t, 3H, J=7.4Hz) |
| 43 | 4-tert-butyl | 1.29(s, 9H) |
| 44 | 2,4,6-trimethyl | 2.24(s, 3H), 2.54(s, 6H) |
| 45 | 4-isopropyl | 1.21(d, 6H, J=6.8Hz), 2.90(quint, 1H, J=6.9Hz) |
| 46 | 4-Cl | 7.67(d, 2H, J=8.6Hz), 7.45(d, 2H, J=8.5Hz) |
| 47 | 3,4-dichloro | 7.82(d, 1H, J=2.0Hz), 7.63–7.57(m, 2H) |
| 48 | 4-F | 7.77–7.74(m, 4H), 7.19(t, 2H, J=8.7Hz) |
| 49 | 4-CF$_3$ | 7.89(d, 2H, J=8.3Hz), 7.77(d, 2H, J=8.3Hz) |
| 50 | 3,5-bistrifluoromethyl | 8.18(s, 2H), 8.15(s, 1H) |
| 51 | 2-Cl | 7.99(dd, 1H, J=1.5, 8.7Hz), 7.53–7.49(m, 2H), 7.37(m, 1H) |
| 52 | 2-NO$_2$ | 7.85(d, 1H, J=7.9Hz), 7.76(d, 1H, J=7.9Hz), 7.69(t, 1H, J=7.7Hz), 7.61(t, 1H, J=7.7Hz) |
| 53 | 3-NO$_3$ | 8.50(t, J=2.0Hz), 8.37(dt, 1H, J=1.1, 8.2Hz), 8.04(dd, 1H, J=1.6, 7.9Hz), 7.71(t, 1H, J=8.0Hz) |
| 54 | 4-NO$_2$ | 8.30(d, 2H, J=8.9Hz), 7.93(d, 2H, J=9.0Hz) |
| 55 | 2-F | 7.79(dt, 1H, J=1.8, 7.8Hz), 7.58(m, 1H), 7.26–7.21(m, 2H) |
| 56 | 3-CF$_3$ | 7.98–7.95(m, 2H), 7.86(d, 1H, J=7.9Hz), 7.68(t, 1H, J=7.5Hz) |
| 57 | 3-Cl | 7.70(t, 1H, J=1.9Hz), 7.61(dt, 1H, J=1.3, 8.0Hz), 7.54(dq, 1H, J=1.1, 8.0Hz), |

TABLE 1-continued

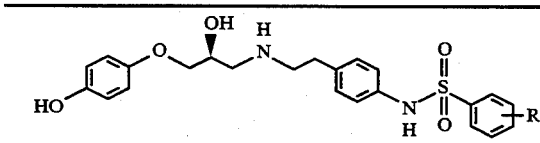

| Example | R | Selected ¹H NMR (CD₃OD) Data |
|---|---|---|
| 58 | 3-Me | 7.43(t, 1H, J=8.0Hz) 7.54(br s, 1H), 7.50(d, 1H, J=8.2Hz), 7.36–7.29(m, 2H) |
| 59 | 2,3,4,5,6-pentamethyl | 2.52(s, 6H), 2.23(s, 3H), 2.18(s, 6H) |
| 60 | 4-Ph | 7.78(d, 2H), 7.70(d, 2H), 7.60(d, 2H), 7.43(t, 2H), 7.37(t, 3H) |
| 61 | 2,5-dichloro | 7.95(s, 1H), 7.50(s, 2H) |
| 62 | 2,4-dichloro | 7.94(d, 1H, J=8.5Hz), 7.58(s, 1H), 7.38(d, 1H, J=8.6Hz) |
| 63 | 2,3-dichloro | 7.96(d, 1H, J=8.0Hz), 7.70(d, 1H, J=8.0Hz), 7.35(t, 1H, J=8.1Hz) |
| 64 | 4-CN | 7.85(d, 2H, J=8.6Hz), 7.81(d, 2H, J=8.7Hz) |
| 65 | 2-Cl, 3-F | 7.81(d, 1H, J=6.8Hz), 7.67–7.63(m, 1H), 7.33(t, 1H, J=8.8Hz) |
| 66 | 3,4-dibromo | 7.93(s, 1H), 7.77(d, 1H, J=8.4Hz), 7.52(d, 1H, J=8.5Hz) |
| 67 | 2,6-dichloro | 7.45(d, 2H, J=7.7Hz), 7.35(t, 1H, J=7.2Hz) |
| 68 | 3,5-dichloro | 7.61(s, 3H) |
| 69 | 3,4-dimethoxy | 3.82(s, 3H), 3.74(s, 3H) |
| 70 | 2-CF₃ | 8.03(d, 1H, J=7.5Hz, 7.89(d, 1H, J=7.5Hz), 7.70–7.64(m, 2H) |
| 71 | 2,3,5,6-tetramethyl | 7.14(s, 1H), 2.49(s, 6H), 2.22(s, 6H) |
| 72 | 4-Br | 7.62(d, 2H, J=9.0Hz), 7.59(d, 2H, J=9.0Hz) |
| 73 | 4-OH | 7.55(d, 1H, J=8.8Hz), 6.77(overlapping d, 4H) |
| 74 | 4-NHCOMe | 2.12(s, 3H) |
| 75 | 4-NHCOEt | 2.38(q, 2H, J=8Hz), 1.18(t, 3H, J=8Hz) |
| 76 | 4-NHCOCHMe₂ | 2.63–2.57(m, 1H), 1.27(d, 6H, J=7.2Hz) |
| 77 | 4-NHCO-nHex | 2.35(t, 2H, J=8Hz), 1.70–1.62(m, 2H), 1.38–1.27(m, 6H), 0.91–0.88(m, 3H) |
| 78 | 4-NHCOCH₂CO₂Me | 3.72(s, 3H), 3.48(s, 2H) |
| 79 | 4-NHCOCH₂CO₂H | 3.42(s, 1H) enol form |
| 80 | 4-NHCO(CH₂)₂CO₂Me | 3.66(s, 3H), 2.68–2.65(m, 4H) |
| 81 | 4-NHCO(CH₂)₂CO₂H | 2.65(s, 4H) |
| 82 | 4-NHCO(CH₂)₃CO₂Me | 3.62(s, 3H), 2.43–2.37(m, 4H), 1.98–1.90(m, 2H) |
| 83 | 4-NHCO(CH₂)₃CO₂H | 2.45(t, 2H, J=8Hz), 2.37(t, 2H, J=8Hz), 1.98–1.90(m, 2H) |
| 84 | 4-NHCO(CH₂)₅CO₂Et | 4.07(q, 2H, J=8Hz), 2.36(t, 2H, J=8Hz), 2.31(t, 2H, J=8Hz), 1.72–1.58(m, 4H), 1.43–1.33(m, 2H), 1.20(t, 3H, J=8Hz) |
| 85 | 4-NHCO(CH₂)₆CO₂Me | 3.61(s, 3H), 2.36(t, 2H, J=8Hz), 2.30(t, 2H, J=8Hz), 1.70–1.55(m, 4H), 1.40–1.30(m, 4H) |
| 86 | 4-NHCOPh | 7.90(d, 2H, J=8Hz), 7.61–7.57(m, 1H), 7.51–7.49(m, 2H) |
| 87 | 4-NHCO₂Me | 3.72(s, 3H) |
| 88 | 4-NHCO₂Et | 4.66(q, 2H, J=8Hz), 1.28(t, 3H, J=8Hz) |
| 89 | 4-NHCO₂CH₂Ph | 7.4–7.27(m, 5H), 5.16(s, 2H) |
| 90 | 4-NHCO₂CHMe₂ | 4.97–4.88(m, 1H), 1.28(d, 6H, J=7.2Hz) |
| 91 | 4-NHCO₂CH₂CO₂Me | 4.68(s, 2H), 3.74(s, 3H) |
| 92 | 4-NHCONH-nPro | 3.13(t, 2H, J=7.2Hz), 1.55–1.48(m, 2H), 0.92(t, 3H, J=8Hz) |
| 93 | 4-NHCONHCHMe₂ | 3.90–3.80(m, 1H), 1.15(d, 6H, J=6.4Hz) |
| 94 | 4-NHCONH-cHex | 3.53(m, 1H), 1.92–1.15(m, 10H) |
| 95 | 4-NHCONH-CH₂CO₂Me | 3.95(s, 2H), 3.72(s, 3H) |
| 96 | 3-NHCOEt | 8.09(s, 1H), 7.69(d, 1H, J=8Hz), 7.34–7.43(m, 2H), 2.37(q, 2H, J=8Hz), 1.17(t, 3H, J=8Hz) |
| 97 | 3-NHCO-nPro | 2.32(t, 2H, J=8Hz), 1.70(m, 2H), 0.97(t, 3H, J=8Hz) |
| 98 | 3-NHCO(CH₂)₄CO₂Me | 3.63(s, 3H), 2.33–2.40(m, 4H), 1.60–1.74(m, 4H) |
| 99 | 3-NHCO(CH₂)₅CO₂Et | 4.09(t, 2H, J=8Hz), 2.32(m, 4H0, 1.67(m, 4H), 1.38(m, 2H), 1.21(t,3H) |
| 100 | 3-NHCOPh | 7.90(s, 2H, J=8Hz), 7.57(m, 1H), 7.45–7.52(m, 2H) |

TABLE 2

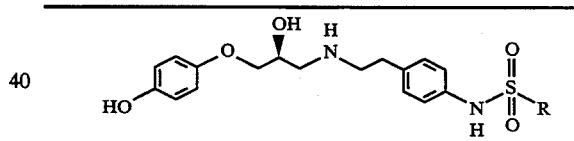

| Example | R | Selected ¹H NMR (CD₃OD) Data |
|---|---|---|
| 101 | Me | 2.89(s, 3H) |
| 102 | Et | 3.02(q, 2H, J=7.4Hz), 1.27(t, 3H, J=7.4Hz) |
| 103 | n-propyl | 1.79(hex, 2H, J=7.7Hz), 0.98(t, 3H, J=7.5Hz) |
| 104 | n-butyl | 1.89(m, 2H), 1.38(hex, 2H, 7.5Hz), 0.88(t, 3H, J=7.3Hz) |
| 105 | CH₂Ph | HBr salt: 7.32–7.24(m, 7H), 4.37(s, 2H) |
| 106 | CH₂CH₂CH₂Ph | 7.24–7.10(m, 9H), 2.07(m, 2H) |
| 107 | naphth-1-yl | 8.72(d, 1H, J=8.3Hz), 8.14(d, 1H, J=7.3Hz), 8.06(d, 1H, J=8.3Hz), 7.95(d, 1H, J=7.5Hz), 7.67(t, 1H, J=6.9Hz), 7.59(t, 1H, J=8.0Hz), 7.47(t, 1H, J=7.5Hz) |
| 108 | thiophen-2-yl | 7.68(dd, 1H, J=0.9, 4.4Hz), 7.45(d, 1H, J=5.3Hz), 7.04(m, 1H) |
| 109 | pyridin-2-yl | 8.63(d, 1H, J=5.7Hz), 7.95(m, 2H), 7.54(m, 1H) |
| 110 | pyridin-3-yl | 8.87(d, 1H, J=1.5Hz), 8.74(dd, 1H, J=1.5, 5.1Hz), 8.26(m, 1H), 7.67(dd, 1H, J=5.1, 8.2Hz) |
| 111 | 2-methylthio- | 8.09(d, 1H, J=2.8Hz), |

TABLE 2-continued

[Structure: HO-phenyl-O-CH2-CH(OH)-CH2-NH-CH2CH2-phenyl-NH-SO2-R]

| Example | R | Selected $^1$H NMR (CD$_3$OD) Data |
|---|---|---|
|  | benzothiazol-5-yl | 7.95(d, 1H, J=8.4Hz), 7.69(dd, 1H, J=2.8, 8.4Hz), 2.79(s, 3H) |
| 112 | quinolin-6-yl | 8.95(dd, 1H, J=1.7, 4.3Hz), 8.42(d, 1H, J=8.4Hz), 8.37(d, 1H, J=2.0Hz), 8.01(dd, 1H, J=2.0, 9.0Hz), 7.61(dd, 1H, J=4.3, 8.4Hz) |
| 113 | 1,2,3,4-tetrahydro-quinolin-6-yl | 7.71(m, 1H), 7.46(m, 1H), 7.19(s, 1H), 3.50(m, 2H), 2.80(m, 1H), 2.13(m, 2H), 1.97(m, 1H) |
| 114 | indolin-5-yl | 7.32(m, 2H), 6.42(d, 1H, J=8.2Hz), 3.52(t, 2H, J=8.7Hz), 2.90(t, 2H, J=8.7Hz) |
| 115 | 1-acetylindolin-5-yl | 8.09(d, 1H, J=8.6Hz), 7.55(m, 2H), 4.12(t, 2H, J=8.7Hz), 3.16(t, 2H, J=8.7Hz), 2.20(s, 3H) |
| 116 | 3-acetylindolin-5-yl | 8.30(overlapping s, 1H, and d, 1H, J=8.4Hz), 7.81(d, 1H, J=1.7Hz), 7.57(dd, 1H, J=1.7, 8.4Hz), 2.50(s, 3H) |
| 117 | oxindol-5-yl | 7.61(m, 2H), 6.88(d, 1H, J=8.8Hz), 3.34(s, 2H) |
| 118 | indol-5-yl | 8.00(d, 1H, J=1.7Hz), 7.47(dd, 1H, J=1.7, 8.6Hz), 7.40(d, 1H, J=8.6Hz), 7.33(d, 1H, J=3.3Hz), 6.52(d, 1H, J=3.3Hz) |
| 119 | benzothiophen-5-yl | 8.04(d, 1H, J=5.9Hz), 7.97(d, 1H, J=5.9Hz), 7.51(d, 1H, J=7.4Hz), 7.37(m, 2H) |
| 120 | benzothiophen-2-yl | 7.86(apparent t, 2H), 7.72(s, 1H), 7.41(m, 2H) |
| 121 | benzofuran-2-yl | 7.64(d, 1H, J=7.8Hz), 7.52(d, 1H, J=8.3Hz), 7.43(apparent dt, 1H, J=1.3, 7.2Hz), 7.30(m, 2H) |
| 122 | 5,6,7,8-tetrahydro-naphth-2-yl | 7.40(m, 2H), 7.11(s, 1H), 2.76(m, 4H), 1.73(m, 4H) |
| 123 | 1,3-benzodioxol-5-yl | 7.29(dd, 1H, J=8, 2Hz), 6.83(d, 1H, J=8Hz), 6.01(s, 2H) |
| 124 | 1,4-benzodioxan-6-yl | 7.19(m, 2H), 6.85(d, 1H, J=8Hz), 4.21(m, 4H) |
| 125 | 1,2-benzisoxazol-5-yl | 7.8(m, 2H), 6.95(d, 1H, J=8Hz) |
| 126 | 2,3-dihydrobenzofuran-5-yl | 7.56(s, 1H), 7.49(dd, 1H, J=8.5, 2Hz), 4.8(t, 2H, J=9Hz), 3.19(t, 2H J=9Hz) |

EXAMPLE 127

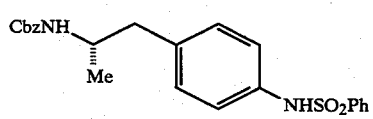

(S)-N-[4-[2-[(phenylmethoxycarbonyl)amino]propyl]-phenyl]benzenesulfonamide

A slurry of 3.00 g (16.6 mmol) of 4-amino-D-phenylalanine hydrate in 100 mL of methanol was heated at relux while gaseous hydrogen chloride was bubbled into the flask. After a 2-h period, the reaction mixture was cooled to room temperature, flushed with nitrogen, and concentrated. The residue was dissolved in 120 mL of a mixture of 140 mL of tetrahydrofuran (THF) and 50 mL of water and treated with 9.15 g (49.8 mmol) of sodium bicarbonate portionwise over a 20-min period. A solution of 18 g of di-tert-butyl dicarbonate in remaining 70 mL of the THF-water mixture was added. The reaction mixture was allowed to stir at room temperature overnight and then was filtered and concentrated. The residue was partitioned between water and dichloromethane. The organic phase was dried over magnesium sulfate and concentrated. Purification by flash chromatography gave 5.17 g (79%) of the corresponding N-Boc methyl ester.

A 4.28-g (10.9 mmol) portion of the above compound was dissolved in 50 mL of THF and treated with 11 mL (22 mmol) of a 2 M lithium borohydride solution in THF. After the reaction mixture was allowed to stir overnight, it was quenched by the addition of 5 mL of saturated aqueous ammonium chloride solution and concentrated. The residue was partitioned between water and ethyl acetate. The aqueous phase was extracted with ethyl acetate and the combined organic phases were dried over magnesium sulfate and concentrated. The resultant material was dissolved in 50 mL of dichloromethane, cooled to 0° C., and treated with 1.8 mL of triethylamine and 0.90 mL of methanesulfonyl chloride. After the reaction mixture was allowed to stir at 0° C. for 1 h, it was washed sequentially with 5% aqueous hydrochloric acid and saturated aqueous sodium bicarbonate, dried over magnesium sulfate, s and concentrated. The resultant semisolid was immediately dissolved in 150 mL of dichloromethane and treated with 30 mL of trifluoroacetic acid. After 1.5 h, the solution was concentrated. The residue was dissoved in 70 mL of ethanol and 5.0 g (49 mmol) of sodium acetate was added. The mixture was stirred over 1 g of 20% palladium hydroxide on carbon under hydrogen at 30 psi for 24 h. It was filtered through Celite and concentrated. Flash chromatography (4:1 dichloromethane: 10% concentrated ammonium hydroxide in methanol) to give 2.01 g of (2S)-1-(4-aminophenyl)propyl-2-amine.

A 451 mg (3.0 mmol) portion of the above compound was is dissolved in 20 mL of chloroform and 2 mL of DMF and cooled to 0° C. Triethylamine (304 mg, 0.420 mL, 3.0 mmol) was added followed by 512 mg (0.428 mL, 3.0 mmol) of benzyl chloroformate, dropwise. The reaction mixture was allowed to stir at 0° C. for 2 h and then allowed to warm to room temperature overnight. It was then partitioned between ethyl acetate and water. The organic phase was dried over magnesium sulfate and concentrated. Purification by flash chromatography (silica gel, 50% ethyl acetate/hexanes) gave 138 mg of the corresponding N-Cbz derivative. This compound was treated with benzenesulfonyl chloride according to the procedure described in Example 5 to give the s title compound: $^1$H NMR (400 MHz, CDCl$_3$) 7.70 (d, 2H, J=7.5 Hz), 7.2–7.5 (m, 8H), 7.00 (d, 2H, J=8.2 Hz), 6.93 (d, 2H, J=8.2 Hz), 6.48 (s, 1H), 5.03 (s, 2H), 4.51 (m, 1H), 3.88 (m, 1H), 2.73 (m, 1H), 2.60 (dd, 1H, J=6.8,

EXAMPLE 128

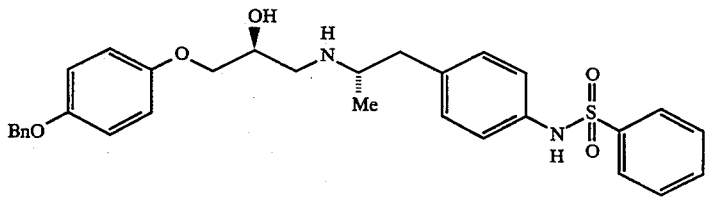

(S,S)-N-[4-[2-[[2-hydroxy-3-[(4-phenylmethoxy)-phenoxy]propyl]amino]propyl]phenyl]benzenesulfonamide The Cbz amine from Example 127 was deprotected as described in Example 6. In a manner analogous to that of Example 7, the title compound was prepared from the resultant amine and the epoxide from Example 1: $^1$H NMR (400 MHz, CD$_3$OD) 7.70 (d, 2H, J =7.1 Hz), 7.52 (m, 1H), 7.2–7.5 (m, 7H), 7.06 (d, 2H, J=8.6 Hz), 7.00 (d, 2H, J=8.6 Hz), 6.75 (d, 2H, J=9.0), 6.68 (d, 2H, J=9.0 Hz), 5.02 (s, 2H), 3.95 (m, 1H), 3.83 (d, 2H, J=5.1 Hz), 2.85 (m, 2H), 2.67 (dr, 1H, J=6.8, 13.2 Hz), 2.56 (m, 2H), 1.03 (d, 3H, J=6.3 Hz). FAB MS m/z 547 (M+1).

EXAMPLE 129

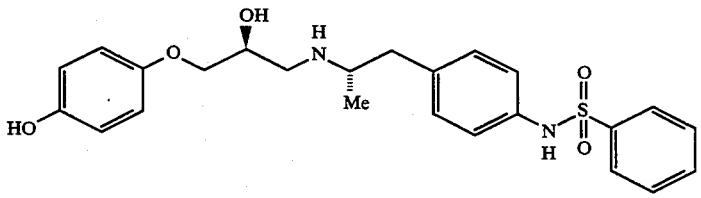

(S,S)-N-[4-[2-[[2-hydroxy-3-(4-hydroxyphenoxy)-propyl]amino]propyl]phenyl]benzenesulfonamide In a manner analogous to that of Example 8, the title compound was prepared from the benzyl ether from Example 128: $^1$H NMR (400 MHz, CD$_3$OD) 7.71 (d, 2H, J=7.2 Hz), 7.52 (m, 1H), 7.43 (m, 2H), 7.06 (d, 2H, J=8.6 Hz), 7.00 (d, 2H, J=8.6 Hz), 6.75 (d, 2H, J=9.0), 6.68 (d, 2H, J=9.0 Hz), 3.93 (m, 1H), 3.82 (d, 2H, J=5.2 Hz), 2.88 (m, 2H), 2.66 (dd, 1H, J=6.6, 13.2 Hz), 2.57 (m, 2H), 1.04 (d, 3H, J=6.3 Hz). FAB MS m/z 457 (M+1).

EXAMPLE 130

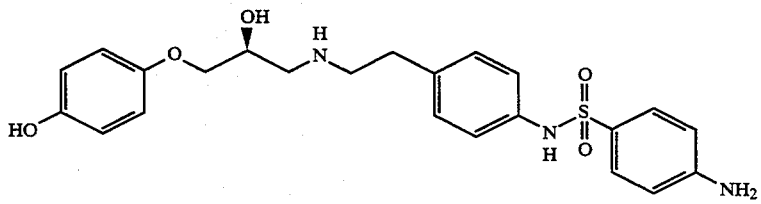

(S)-N-[4-[2-[[2-hydroxy-3-(4-hydroxyphenoxy)propyl-]amino]ethyl]phenyl]-4-aminobenzenesulfonamide A solution of 67 mg (0.14 mmol) of nitro derivative from Example 54 in 5 mL of methanol was stirred over 20% palladium hydroxide on carbon under an atmosphere of hydrogen for 30 min. The reaction mixture was filtered and concentrated to give 36 mg (59%) of the title compound: $^1$H NMR (400 MHz, CD$_3$OD) δ7.39 (d, 2H, J=8.8 Hz), 7.08 (d, 2H, J=8.5 Hz), 7.00 (d, 2H, J=8.5 Hz), 6.75 (d, 2H, J=9.1 Hz), 6.68 (d, 2H, J=9.0 Hz), 6.56 (d, 2H, J=8.8 Hz), 4.04 (m, 1H), 3.89–3.82 (overlapping dd, 2H), 2.97–2.77 (m, 6H).

EXAMPLE 131

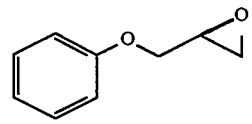

(S)-2-phenoxymethyloxirane

The title compound was prepared from phenol in a manner analogous to that of Example 1: $^1$H NMR (400 MHz, CDCl$_3$) δ7.28 (t, 2H), 6.96 (t, 1H), 6.91 (d, 2H), 4.20 (dd, 1H), 3.96 (dd, 1H), 3.34 (m, 1H), 2.90 (t, 1H), 2.73 (dd, 1H).

EXAMPLE 132

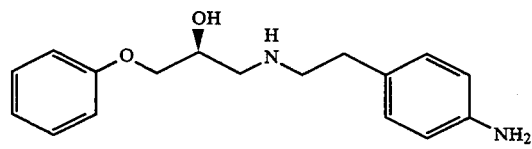

(S)-N-[2-[4-(aminophenyl)]ethyl]-2-hydroxy-3-phenoxypropylamine

In a manner analogous to that of Example 7, the title compound was prepared from the epoxide from Example 131 and 2-(4-aminophenyl)ethylamine: $^1$H NMR (400 MHz, CDCl₃) δ7.25 (t, 2H, J =8.0 Hz), 6.97 (d, 2H, J=8.4 Hz), 6.93 (t, 1H, J=7.4 Hz), 6.87 (d, H, J=7.8 Hz), 6.61 (d, 2H, J=8.4 Hz), 4.00 (m, 1H), 3.93 (d, 2H, J=5.4 Hz), 3.57 (br s, 1H), 2.90–2.71 (m, 6H), 1.85 (br s, 3H).

EXAMPLE 133

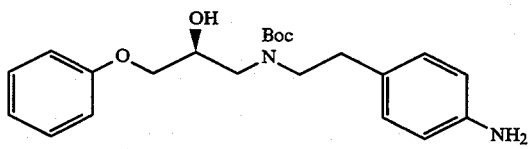

(S)-N-[2-[4-(aminophenyl)]ethyl]-2-hydroxy-3-phenoxypropylcarbamic acid 1,1-dimethylethyl ester In a manner analogous to that of Example 33, the title compound was prepared from the amine from Example 132 and di-tertbutyldicarbonate: ¹H NMR (400 MHz, CDCl₃) δ7.26 (t, 2H, J=8.0 Hz), 6.96–6.87 (m, 5H), 6.59 (d, 2H, J=8.4 Hz), 4.10 (br m, 1H), 3.94 (br m, 1H), 3.84 (br m, 1H), 3.56 (br s, 1H), 3.45–3.20 (m, 4H), 2.78 (br m, 2H), 1.55 (br s, 3H), 1.43 (s, 9H).

EXAMPLE 134

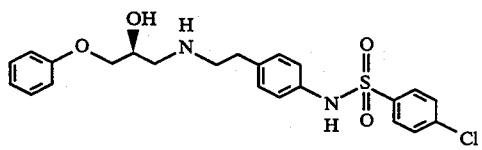

(S)-N-[4-[2-[(2-hydroxy-3-phenoxypropyl)amino]ethyl]phenyl]-4-chlorobenzenesulfonamide To a solution of the BOC-protected aniline from Example 133 (96 mg, 0.25 mmol) and pyridine (50 gL, 0.6 mmol) in 5 mL of methylene chloride was added 4-chlorobenzenesulfonyl chloride (57 mg, 0.27 mmol). The reaction mixture was stirred at room temperature under nitrogen atmosphere overnight. The red solution was concentrated under vacuum and the residue was purified by preparative thin layer chromatography on silica gel (eluant 2:3 ethyl acetate/hexanes) to give 133 mg (98%) of an off-white solid. This NBOC sulfonamide (130 mg, 0.227 mmol) was dissolved in 3 mL of methylene chloride and 1 mL of trifluoroacetic acid was added. After stirring at room temperature for 1 h, the solution was concentrated and the residue was purified by preparative thin layer chromatography on silica gel (eluant 10:90:1 methanol/methylene chloride/30% ammonium hydroxide) to give 130 mg (99%) of the title compound. ¹H NMR (400 MHz, CD₃OD) δ7.71 (d, 2H, J=9Hz), 7.47 (d, 2H, J=9Hz), 7.27 (t, 2H, J=9Hz), 7.16 (d, 2H, J=8.5Hz), 7.07 (d, 2H, J=8.5Hz), 6.94 (dd, 3H), 4.22 (m, 1H), 3.99 (m , 2H), 3.21 (m, 3H), 2.94 (m, 2H).

Following the procedures outlined for Examples 131–134, the compounds listed in Table 3 were prepared.

TABLE 3

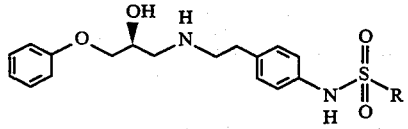

| Example | R | Selected ¹H NMR (CD₃OD) Data |
|---|---|---|
| 135 | Ph | 7.72(d, 2H, J=7.1Hz), 7.52(t, 1H, J=7.3Hz), 7.44(t, 2H, J=7.5Hz) |
| 136 | 4-fluorophenyl | 7.75(dd, 2H, J=5.1, 8.9Hz), 7.17(t, 2H, J=8.8Hz) |
| 137 | 4-bromophenyl | 7.62(d, 2H, J=9.1Hz), 7.59(d, 2H, J=9.1Hz) |
| 138 | 2,3-dihydrobenzofuran-5-yl | 4.56(t, 2H, J=9Hz), 3.15(t, 2H, J=9Hz) |
| 139 | 1-acetylindolin-5-yl | 8.08(d, 1H, J=8.7Hz), 7.52(m, 2H), 4.09(t, 2H, J=8.7Hz), 3.13(t, 2H, J=8.7), 2.18(s, 3H) |
| 140 | benzothiophen-2-yl | 7.87(apparent t, 2H, J=8.1Hz), 7.75(s, 1H), 7.42(m, 2H) |

EXAMPLE 141

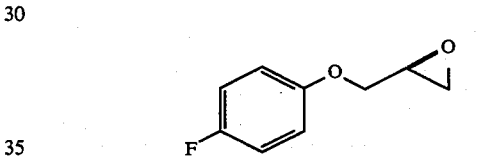

(S)-2-[(4-Fluorophenoxy)methyl]oxirane

The title compound was prepared from 4-fluorophenol in a manner analogous to that of Example 1: ¹NMR (400 MHz, CDCl₃) 6.95 (m, 2H), 6.84 (m, 2H), 4.17 (dd, 1H, J=3.0, 11.0 Hz), 3.88 (dd, 1H, J =5.7, 11.0 Hz), 3.33 (m, 1H), 2.88 (m, 1H), 2.73 (dd, 1H, J=2.6, 5.0 Hz).

EXAMPLE 142

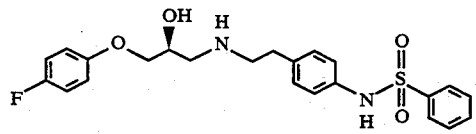

(S)-N-[4-[2-[[3-(4-fluorophenoxy)-2-hydroxypropyl]amino]ethyl]phenyl]benzenesulfonamide In a manner analogous to that of Example 7, the title compound was prepared from the amine from Example 6 and the epoxide from Example 141: ¹H NMR (300 MHz, CD₃OD): 2.93 (m, 2H), 3.1–3.28 (m, 4H), 3.96 (m, 2H), 4.2 (m, 1H), 6.9–7.16 (m, 8H), 7.5 (m, 3H), 7.74 (d, J=7Hz, 1H); FAB-MS m/z 445 (M+1).

Following the procedures outlined for Examples 141–142, the compounds listed in Table 4 were prepared.

TABLE 4

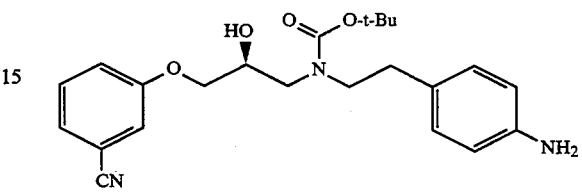

| Example | R | Selected ¹H NMR (CD₃OD) Data |
|---|---|---|
| 143 | 4-methylphenyl | 2.33(s, 3H) |
| 144 | 4-methoxyphenyl | 7.63(d, 2H, J=9.0Hz), 3.79(s, 3H) |
| 145 | 4-nitrophenyl | 8.29(d, 2H, J=9.0Hz), 7.91(d, 2H, J=9.0Hz) |
| 146 | 4-bromophenyl | 7.62(d, 2H, J=9.1Hz), 7.67(d, 2H, J=9.1Hz) |
| 147 | 4-iodophenyl | 7.82(d, 2H, J=8.7Hz), 7.43(d, 2H, J=8.7Hz) |
| 148 | quinolin-3-yl | 9.01(d, 1H, J=2.3Hz), 8.71(d, 1H, J=2.0Hz), 8.06(d, 1H, J=8.4Hz), 8.02(d, 1H, J=8.4Hz), 7.91(apparent td, 1H), 7.71(apparent t, 1H) |
| 149 | 1,3-benzodioxol-5-yl | 7.27(dd, 1H, J=7.2Hz), 6.97(d, 1H, J=7Hz) |

EXAMPLE 150

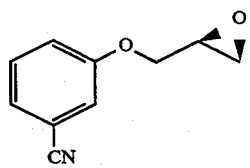

(S)-2-[[3-Cyanophenoxy]methyl]oxirane

The title compound was prepared from 3-cyanophenol in a nanner analogous to that of Example 1: ¹NMR (400 MHz, CDCl₃) δ7.35 (t, 1H), 7.24 (d, 1H), 7.13 (m, 2H), 4.27 (dd, 1H, J=2.7, 11.1 Hz), 3.89 (dd, 1H, J=6.0, 11.1 Hz), 3.33 (m, 1H), 2.90 (t, 1H), 2.75 (dd, 1H, J=2.6, 4.8Hz).

EXAMPLE 151

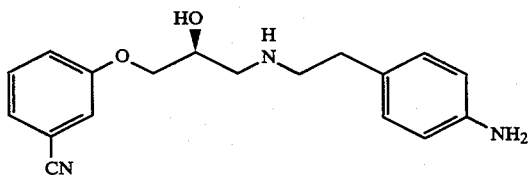

(S)-N-[4-[2-[[2-Hydroxy-3-(3-cyanophenoxy)propyl]amino]ethyl]phenyl]amine

In a manner analogous to that of Example 7, the title compound was prepared from 2-(4-aminophenyl)ethylamine and the epoxide from Example 150: ¹NMR (400 MHz, CD₃OD) δ7.44 (t, 1H), 7.27 (m, 3H), 6.97 (d, 2H, J=8.5Hz), 6.67 (d, 2H, J=8.4Hz), 4.04 (m, 1H), 3.97 (m, 2H), 2.81 (m, 3H), 2.71 (m, 3H).

EXAMPLE 152

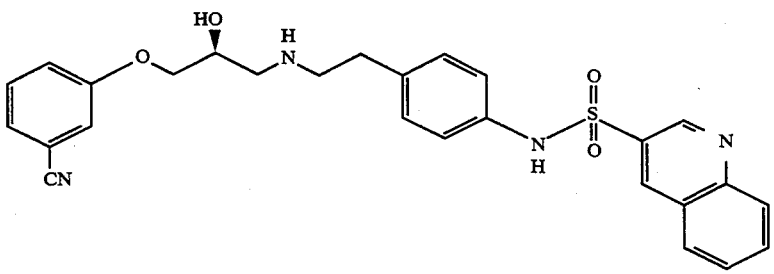

(S)-N-[2-[4-(Aminophenyl)]ethyl]-2-hydroxy-3-(3-cyanophenoxy)propylcarbamic acid 1,1-dimethylethyl ester In a manner analogous to that of Example 33, the title compound was prepared from the amine in the previous Example 151 and di-tert-butyldicarbonate: NMR (400 MHz, CD₃OD) δ7.44 (t, 1H), 7.27 (m, 3H), 6.99 (d, 2H), 6.65 (d, 2H), 4.08 (m, 1H), 3.92 (m, 2H), 3.43 (m, 3H), 3.15 (m, 1H), 2.70 (t, 2H), 1.42 (s, 9H).

EXAMPLE 153

(S)-N-[4-[2-[[2-Hydroxy-3-(3-cyanophenoxy)propyl]amino]ethyl]phenyl]-3-quinolinesulfonamide In a manner analogous to that of Example 134, the title compound was prepared from the amine from Example 152 and 3-quinolinesulfonyl chloride from Example 34. The crude product treated with trifluoroacetic acid to remove Boc group: NMR (400 MHz, CD₃OD) δ9.01 (d, 1H, J=2.2Hz), 8.69 (d, 1H, J=2.2Hz), 8.05 (dd, 2H), 7.90 (t, 2H), 7.70 (t, 1H), 7.42 (t, 1H), 7.26 (m, 3H), 7.06 (dd, 4H, J=8.6, 21.6 Hz), 4.03 (m, 1H), 3.96 (m, 2H), 2.82 (m, 3H), 2.73 (m, 3H). FAB-MS m/z 503 (M+1).

EXAMPLE 154

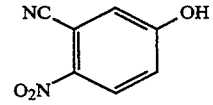

3-Cyano-4-nitrophenol

To a 0° C. solution of 578 mg (2.28 mmol) 5-phenylmethoxy-2-nitrobenzonitrile, prepared according to the procedure of E. Elslager, et. al., *J. Heterocyclic Chem.* 1972, 9, 759–773, in 5 mL of dichloromethane at 0° C. was added 2.6 mL (2.62 mmol, 1.15 equiv) of a 1.0 M solution of boron tribromide in dichloromethane. After the reaction mixture was stirred for 3 h, it was diluted with ethyl acetate, washed sequentially with 1N aqueous sodium hydrogen sulfate solution and saturated aqueous sodium chloride solution, dried over magnesium sulfate and concentrated to give 357 mg (96%) of the title compound which was used without further purification: $^1$H NMR (400 MHz, CD$_3$OD) δ8.17 (d, 1H, J=9.2 Hz), 7.03 (d, 1H, J=2.7 Hz), 6.92 (dd, 1H, J=2.7, 9.3 Hz).

EXAMPLE 155

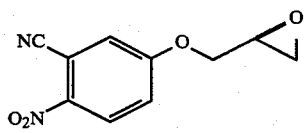

(S)-2-[(3-Cyano-4-nitrophenyl)methyl]oxirane

To a solution of 357 mg (2.18 mmol) of 3-cyano-4-nitrophenol from Example 154 in 5 mL of DMF at 0° C. was added 91.0 mg (2.28 mmol) of sodium hydroxide as a 60% dispersion in oil. After the mixture was allowed to stir for 30 min, a solution of 513 mg( 1.98 mmol) of (2S)-glycidyl 3-nitrobenzene sulfonate in 10 mL of DMF was added via cannula. The reaction mixture was allowed to warm to room temperature and then heated at 55° C. overnight. The reaction was cooled, quenched by the addition of saturated aqueous ammonium chloride solution, and poured into ethyl acetate. The organic phase was washed sequentially with two portions of water and one portion of saturated aqeous sodium chloride solution. The organic phase was dried over magnesium sulfate and concentrated. Purification by flash chromatography (silica, 40% ethyl acetate/hexanes) gave 287 mg (66%) of the title compound as a yellow solid: $^1$H NMR (400 MHz, CDCl$_3$) δ8.29 (d, 1H, J=9.2 Hz), 7.36 (d, 1H, J=2.8 Hz), 7.25 (dd, 1H, J=2.8, 9.2 Hz), 4.47 (dd, 1H, J=2.3, 11.3), 4.00 (dd, 1H, J=6.2, 11.4 Hz), 3.37 (m, 1H), 2.95 (t, 1H, J=4.3 Hz), 2.77 (dd, 1H, J=2.6, 4.7 Hz).

EXAMPLE 156

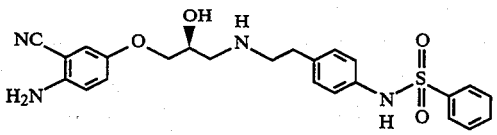

(S)-N-[4-[2-[[3-(4-Amino-3-cyanophenoxy)-2-hydroxypropyl]amino]phenyl]benzenesulfonamide A solution of 75 mg (0.341 mmol) of the epoxide from Example 155 and 122 mg (0.443 mmol, 1.3 equiv) of amine from Example 6 were heated in methanol at reflux overnight. The mixture was concentrated. Purification by flash chromatography (silica, 5% methanol: dichloromethane) gave 48 mg (28%) of the resultant amino alcohol. This was dissoved in ethanol and treated with 10% palladium on carbon under an atmosphere of hydrogen for 6 h. The reaction mixture was filtered and concentrated. Purification by flash chromatography (silica, 5% 10:1 methanol: concentrated aqueous ammonium hydroxide in dichloromethane) gave 15 mg of the title compound: $^1$H NMR (400 MHz, CDCl$_3$) δ7.71 (d, 2H, J=7.2 Hz), 7.53 (t, 1H, J=7.4 Hz), 7.44 (t, 2H, J=7.6 Hz), 7.07 (d, 2H, J=8.6 Hz), 7.01–6.98 (m, 3H), 6.90 (d, 1H, J=2.8 Hz), 6.77 (d, 1H, J=9.0 Hz).

EXAMPLE 157

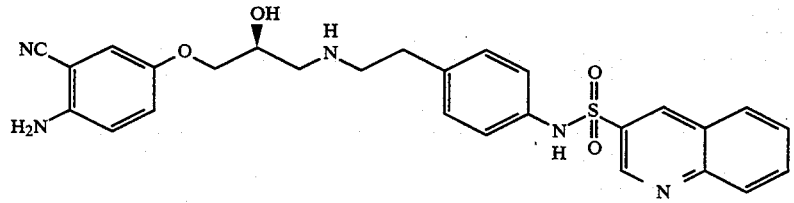

(S)-N-[4-[2-[[3-(4-Amino-3-cyanophenoxy)-2-hydroxypropyl]amino]ethyl]phenyl]-3-quinolinesulfonamide In a manner analogous to that of Example 156, the title compound was prepared from the epoxide from Example 155 and N-[4-(2-aminoethyl)phenyl]-3-quinolinesulfonamide: $^1$H NMR (400 MHz, CD$_3$OD) δ9.01 (d, 1H, J=2.3 Hz), 8.69 (d, 1H, J=2.3 Hz), 8.06 (d, 1H, J=8.5 Hz), 8.02 (d, 1H, J=8.5 Hz), 7.90 (m, 1H), 7.70 (m, 1H), 7.11 (d, 2H), 7.04 (d, 2H), 6.98 (dd, 1H), 6.89 (d, 1H, J=3.0 Hz), 6.76 (d, 1H, J=9.0 Hz), 3.98 (m, 1H), 3.82 (d, 2H, J=5.5 Hz), 2.91–2.71 (m, 6H).

EXAMPLE 158

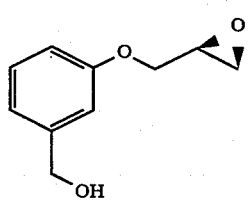

(S)-2-[[3-(Hydroxymethyl)phenoxy]methyl]oxirane

The title compound was prepared from 3-hydroxybenzyl alcohol in a manner analogous to that of Example 1: $^1$NMR (400 MHz, CDCl$_3$) a 7.26 (m, 1H), 6.94 (m, 2H), 6.82 (d, 1H), 4.65 (s, 2H), 4.22 (dd, 1H, J=3.2, 11.0 Hz), 3.95 (dd, 1H, J=5.6, 10.7 Hz), 3.33 (m, 1H), 2.90 (t, 1H), 2.75 (m, 1H).

EXAMPLE 159

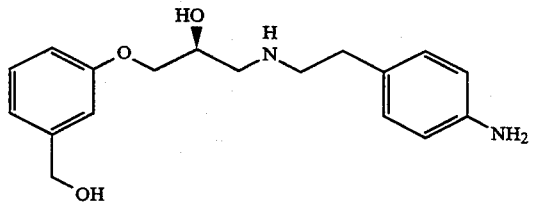

(S)-N-[4-[2-[[2-Hydroxy-3-[(3-hydroxymethyl)phenoxy]propyl]amino]ethyl]phenyl]amine In a manner analogous to that of Example 7, the title compound was prepared from 2-(4-aminophenyl)ethylamine and the epoxide from Example 158 above: NMR (400MHz, CD$_3$OD) δ7.22 (t, H), 6.98 (d, 2H, J=4.4Hz), 6.96 (d, 2H), 6.81 (d, 1H), 6.67 (d, 2H, J=4.4 Hz), 4.56 (s, 2H), 4.08 (m, 1H), 3.92 (d, 2H, J=5.4 Hz), 2.90 (m, 3H), 2.71 (m, 3H).

EXAMPLE 160

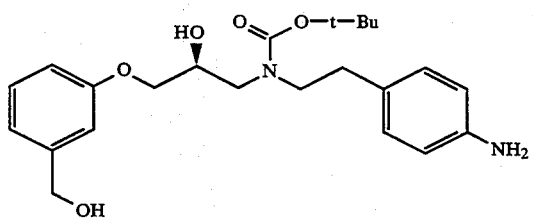

(S)-N-[2-[4-(Aminophenyl)]ethyl]-2-hydroxy-3-[(3-hydroxymethyl)phenoxy]propylcarbamic acid 1,1-dimethylethyl ester In a manner analogous to that of Example 33, the title compound was prepared from the amine from Example 159 and di-tertbutyldicarbonate: NMR (400MHz, CD$_3$OD) δ7.21 (t, 1H), 7.09 (m, 1H), 6.92 (m, 3H), 6.81 (m, 1H), 6.66 (d, 2H), 4.57 (s, 2H), 4.07 (m, 1H), 3.89 (m, 2H), 3.43 (m, 2H), 3.20 (m, 2H), 2.69 (t, 2H), 1.40 (s, 9H).

EXAMPLE 161

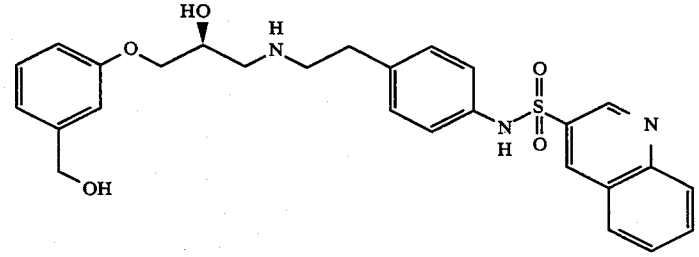

(S)-N-[4-[2-[[2-Hydroxy-3-[(3-hydroxymothyl)phenoxy]propyl]ethyl]phenyl]-3-quinolinesulfonamide In a manner analogous to that of Example 134, the title compound was prepared from the amine from Example 160 and 3quinolinesulfonyl chloride from Example 34. The crude product was treated with trifluoroacetic acid to remove the Boc group: NMR (400 MHz, CD$_3$OD) δ9.01 (d, 1H, J=2.3Hz), 8.68 (d, 1H, J=2.3Hz), 8.04 (dd, 2H), 7.91 (t, 2H), 7.69 (t, 1H), 7.21 (t, 1H), 7.06 (q, 4H), 6.91 (nm, 2H), 6.79 (m, 1H), 4.55 (s, 2H), 4.03 (m, 1H), 3.91 (d, 2H, J=6.6Hz), 2.87 (m, 3H), 2.78 (m, 3H). FAB-MS m/z 508 (M+1).

EXAMPLE 162

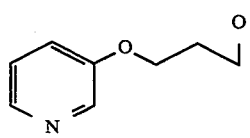

(S)-2-(3-pyridyloxymethyl)oxirane

To a solution of 11.9 g (0.125 mol) of 3-hydroxypyridine in 50 mL of DMSO at 15° C. was added 120 mL (0.12 mol) of a 1.0 M solution of sodium hexamethyldisilylazide in THF. After the reaction mixture was allowed to stir for 5 min, 25.9 g (0.10 mol) of (2S)-glycidyl 3-nitrobenzene sulfonate was added in one portion. The mixture was cooled with a room temperature water bath for 30 min. It s was then quenched by the addition of 250 mL of water and extracted with three portions of ethyl acetate. The combined aqueous extracts were washed sequentially with water and brine, dried over sodium sulfate, treated with granular charcoal, filtered and concentrated to give 7.7 g (51%) of an orange oil which was used without further purification. An analytical sample was prepared by flash chromatography (silica gel, 80% ethyl acetate/hexane): $^1$H NMR (400 MHz, CDCl$_3$) a 8.31 (m, 1H), 8.21 (m, 1H), 7.20–7.22 (m, 2H), 4.29 (dd, 1H, J=1,6 Hz), 3.95 (m, 1H), 3.34 (m, 1H), 2.90 (t, 1H, J=3Hz), 2.75 (m, 1H).

EXAMPLE 163

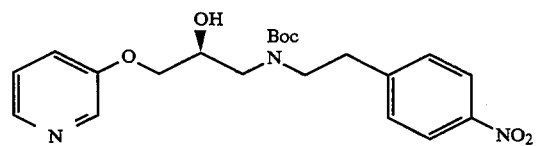

(S)-N-[2-[4-(nitrophenyl)]ethyl]-2-hydroxy-3-pyridinyloxypropylcarbamic acid 1,1-dimethylethyl ester A solution of 34.6 g (0.224 mol) of epoxide from Example 162 in 300 mL of anhydrous methanol was treated with 38 mL (0.275 mol) of triethylamine and 55.7 g (0.275 mol) of 4-nitrophenethylamine hydrochloride. The solution was heated at reflux for 10 h, then cooled to room temperature and concentrated. The resultant mixture was suspended in 500 mL of dichloromethane and treated with 115 g of di-tert-butyldicarbonate in three portions (90 g, 15 g, 10 g) over 4 h. The reaction mixture was stirred overnight. Dilute brine was added and the mixture was extracted three times with dichloromethane. The combined organic extracts were dried over sodium sulfate and concentrated. Purification by flash chromatography (silica gel, 50%, 75%, 100% ethyl acetate/hexane) gave 38.0 g of the title compound: $^1$H NMR (400 MHz, CD$_3$OD) δ8.23 (d, 1H, J=4Hz), 8.12 (dd, 1H, J=2.4Hz), 7.71(d, 2H, J=8Hz), 7.52 (m, 1H), 7.40–7.48 (m, 3H), 7.35 (m, 1H), 7.09 (d, 2H, J=10Hz), 7.00 (d, 2H, J=10Hz), 3.95–4.08 (m, 3H), 2.69–2.90 (m, 6H).

EXAMPLE 164

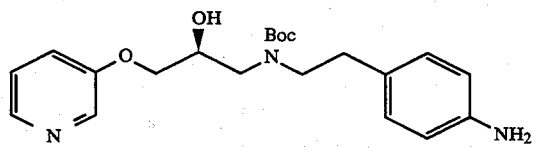

(S)-N-[2-[4-(Aminophenyl)lethyl]-2-hydroxy-3-[(pyridin-3-yl)oxy]propylcarbamic acid 1,1-dimethylethyl ester A 37.8-g (0.09 mol) portion of the nitro compound from Example 163 was dissolved in 300 mL of ethyl acetate and hydrogenated over 7.1 g of 20 % palladium hydroxide on carbon overnight. The mixture was filtered and concentrated to give the title compound, which was used without further purification.

EXAMPLE 165

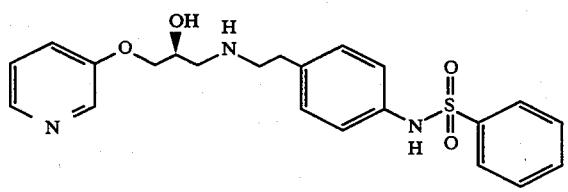

(S)-N-[4-[2-[[2-hydroxy-3-(3-pyridyloxy)propyl]amino]ethyl]phenyl]benzenesulfonamide In a manner analogous to that of Example 7, the title compound was prepared from the epoxide from Example 162 and N-[4-(2-aminoethyl)phenyl]benzenesulfonamide (Example 6). Purification by preparative thin layer chromatography on silica gel (eluant 90:10:2 methylen chloride/methanol/30% ammonium hydroxide) gave the title compound. $^1$H NMR (400 MHz, CD$_3$OD) δ8.23 (d, 1H, J=4Hz), 8.12 (dd, 1H, J=2.4Hz), 7.71(d, 2H, J=8Hz), 7.52 (m, 1H), 7.40–7.48 (m, H), 7.35 (m, 1H), 7.09 (d, 2H, J=10Hz), 7.00 (d, 2H, J=10Hz), 3.95–4.08 (m, 3H), 2.69–2.90 (m, 6H).

EXAMPLE 166

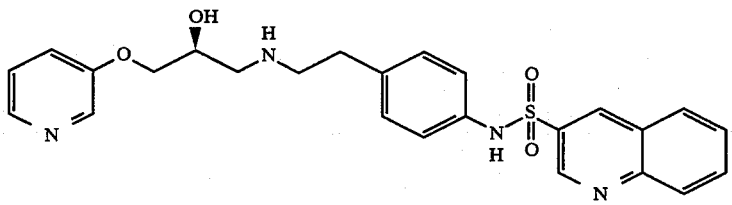

(S)-N-[4-[2-[[2-hydroxy-3-(3-pyridyloxy)propyl]amino]ethyl]-phenyl]3-quinolinesulfonamide To a solution of the aniline (1.0 g, 2.60 mmol) from Example 164 and pyridine (0.21 mL, 2.60 mmol) in 15 mL of methylene chloride was added 3-quinolinesulfonyl chloride (590 mg, 2.60 mmol) from Example 34. The pink solution was stirred at room temperature for 1.5 h and was concentrated under reduced pressure. The residue was dissolved in 20 mL of methanol, and approximately 8 mL of a 6N HCl was added. After warming at reflux for 18 h, the cooled solution was concentrated in vacuo, and the residue was dissolved in 10 mL of 10% methanolic ammonium hydroxide. After removal of solvent in vacuo, the residue was applied directly to a silica gel column. Elution with 9:1 CH$_2$Cl$_2$:10% methanolic NH$_4$OH afforded 0.84 g (1.78 mmol, 68% yield) of the title compound as an yellow solid. NMR (400 MHz, CD$_3$OD) 9.01 (d, 3H, J=2.2 Hz), 8.75 (d, 3H, J=2.2 Hz), 8.22 (d, 3H, J=2.9 Hz), 8.12 (dd, 1H, J=1.3, 4.7 Hz), 8.07 (d, 3H, J=8.6 Hz), 8.04 (d, 3H, J=8.6 Hz), 7.93 (apparent t, 3H), 7.72 (apparent t, 1H), 7.41 (m, 1H), 7.35 (dd, 3H, J=4.7, 7.5 Hz). FAB MS m/z 479 (M +1).

EXAMPLE 167

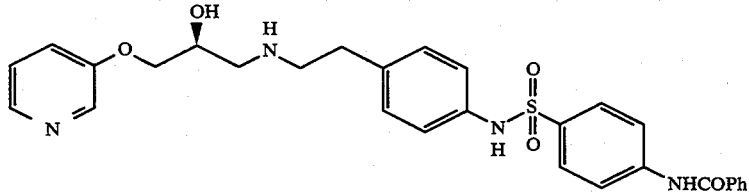

(S)-N-[4-[2-[[2-hydroxy-3-(3-pyridyloxy)propyl]amino]ethyl]-phenyl]-4-benzamidobenzenesulfonamide To a solution of 1.00 g (2.58 mmol) of Boc aniline derivative from Example 164 and 0.25 mL (3.10 mmol, 1.2 equiv) of pyridine in dichloromethane at 0° C. was added a solution of 572 mg (2.58 mmol) of 4-nitrobenzenesulfonyl chloride in 25 mL of dichloromethane via cannula. The reaction mixture was allowed to stir at 0° C. for 1.5 h, then concentrated. Purification by flash chromatography (silica gel, ethyl acetate) gave 1.22 g (84%) of the resultant nitrobenzene sulfonamide. An 820-mg portion was dissolved in 15 mL of ethyl acetate and stirred over 20% palladium hydroxide on s carbon under an atmosphere of hydrogen overnight. The reaction mixture was then filtered and concentrated. Purification by flash chromatography (silica, ethyl acetate) gave 636 mg (80%) of the corresponding 4-aminosulfonamide. A 203-mg (0.374 mrnol) portion was dissolved in 4 mL of dichloromethane and treated with 36 mg (0.036 mL, 0.45 mmol) of pyridine and 58 mg (0.048 mL, 0.41 mmol) of benzoyl chloride. The reaction mixture was allowed to stir at 0° C. for 45 min, and then 4 mL of trifluoroacetic acid was added. After 30 min, the reaction was concentrated. Purification by flash chromatography (silica, 7.5 % 10:1 methanol: concentrated aqueous s ammonium hydroxide in dichloromethane) gave 144 mg (70%) of the title compound: $^1$H NMR (400 MHz, CD$_3$OD) $\delta$8.21 (d, 1H, J=2.9 Hz), 8.11 (dd, 1H, J=1.3, 4.6 Hz), 7.90 (d, 2H, J=7.0 Hz), 7.82 (d, 2H, J=8.9 Hz), 7.69 (d, 2H, J=8.9 Hz), 7.58 (t, 1H, J=7.4 Hz), 7.49 (t, 2H, J=7.4 Hz), 7.40 (ddd, 1H, J=1.3, 2.9, 8.5 Hz), 7.34 (dd, 1H, J =4.5, 8.9 Hz), 7.10 (d, 2H, J=8.5 Hz), 7.02 (d, 2H, J=8.5 Hz), 4.06–3.95 (m, 3H), 2.86–2.69 (m, 6H).

Following the procedures outlined for Examples 162–167, the compounds listed in Tables 5 and 6 were prepared.

TABLE 5

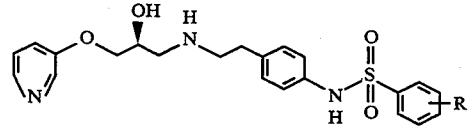

| Example | R | Selected $^1$H NMR (CD$_3$OD) Data |
|---|---|---|
| 168 | 4-Br | 7.60(s, 4H) |
| 169 | 4-I | 7.81(d, 2H, J=8.6Hz), 7.44(d, 2H, J=8.6Hz) |
| 170 | 4-NO$_2$ | 8.27(d, 2H, J=7.0Hz), 7.93(d, 2H, J=6.8Hz) |
| 171 | 4-NH$_2$ | 7.38(d, 2H, J=8.7Hz), 6.56(d, 1H, J=8.7Hz) |
| 172 | 4-NHCOMe | 7.65(d, 2H, J=9.2Hz), 7.62(d, 2H, J=9.2Hz), 2.10(s, 3H) |
| 173 | 4-NHCO$_2$Et | 4.16(q, 2H, J=7.1Hz), 1.27(t, 3H, J=7.1Hz) |
| 174 | 4-NHCO$_2$CHMe$_2$ | 4.08–3.96(m, 4H), 1.26(d, 6H, J=6.2Hz) |
| 175 | 3-NHCO(CH$_2$)$_4$CO$_2$Me | 3.63(s, 3H), 2.33–2.40(m, 4H), 1.60–1.73(m, 4H) |
| 176 | 4-NHCO(CH$_2$)$_4$CO$_2$Me | 3.63(s, 3H), 2.77(q, 2H, J=6.5Hz), 2.36(m, 2H), 1.66(m, 4H) |
| 177 | 4-Propyl | 7.61(d, 2H, J=8.4Hz), 7.26(d, 2H, J=8.5Hz), 2.60(t, 2H, J=7.7Hz), 1.60(hex, 2H, J=7.5Hz), 0.89(t, 3H, J=7.4Hz) |
| 178 | 4-OH | 7.54(d, 2H, J=8.9Hz), 6.76(d, 2H, J=8.9Hz) |
| 179 | 4-OMe | 7.64(d, 2H, J=9.0Hz), 6.95(d, 2H, J=9.0Hz), 3.80(s, 3H) |

TABLE 6

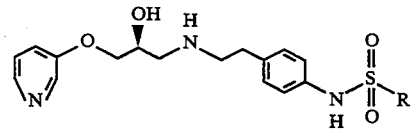

| Example | R | Selected $^1$H NMR (CD$_3$OD) Data |
|---|---|---|
| 180 | CH$_2$CH$_2$Ph | 7.25–7.15(m, 7H), 3.26(m, 2H), 3.03(m, 2H) |
| 181 | 2-methylthio-benzothiazol-5-yl | 8.10(d, 1H, J=2.1Hz), 7.94(d, 1H, J=8.1Hz), 7.65(dd, 1H, J=2.1, 8.1Hz), 2.81(s, 3H) |
| 182 | 1-acetylindolin-5-yl | 8.09(d, 1H), 7.53(m, 2H), 4.13(t, 2H, J=8.8Hz), 3.17(t, 2H, J=8.7Hz), 2.20(s, 3H) |
| 183 | benzofuran-2-yl | 7.62(d, 1H, J=7.6Hz), 7.50(d, 1H, J=8.0Hz), 7.38(m, 1H), 7.24(m, 2H) |
| 184 | benzothiophen-2-yl | 7.88(apparent t, 2H, J=8.0Hz), 7.73(s, 1H), 7.39(m, 2H) |

EXAMPLE 185

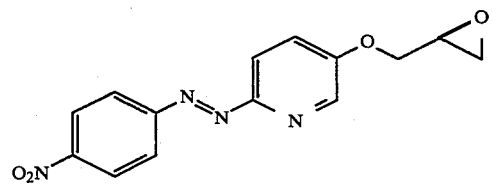

(S)-2-[[[2-(4-nitrobenzenazo)-5-pyridinyl]oxy]methyl]oxirane

The title compound was prepared from 5-hydroxy-2-(4-nitrobenzenazo)pyridine (J. A. Moore and F. J. Marascia, J. Amer. Chem. Soc., 81, 6049–6056 (1959)) in a manner analogous to that of Example 1: $^1$H NMR (400 MHz, CDCl$_3$) $\delta$8.45 (s, 1H), 8.37 (d, 2H, J =9.0 Hz), 8.11 (d, 2H, J=9.0 Hz), 7.94 (d, 1H, J=8.6 Hz), 7.45 (dd, 1H, J=2.9, 8.8 Hz), 4.46 (dd, 1H, J=2.5, 11 Hz), 4.06 (dd, 1H, J=6.0, 11 Hz), 3.41 (m, 1H), 2.96 (t, 1H, J=4.4 Hz), 2.80 (dd, 1H, J=2.6, 4.6 Hz).

EXAMPLE 186

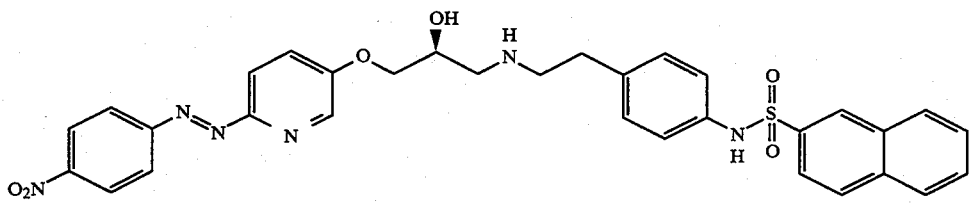

(S)-N-[4-[2-[[2-hydroxy-3-[[2-(4-nitrobenzenazo)-5-pyridinyl]oxy]propyl]amino ethyl]phenyl]-2-naphthalenesulfonamide The Cbz amine from Example 13 was deprotected as described in Example 6. In a manner analogous to that of Example 7, the title compound was prepared from the resultant amine and the epoxide from Example 185: ¹H NMR (400 MHz, CD₃OD) δ8.43 (d, 2H, J=9.0 Hz), 8.38 (d, 1H, J=2.9 Hz), 8.28 (d, 1H, J=1.8 Hz), 8.13 (d, 2H, J=9.0 Hz), 7.98 (d, 1H, J=9.0 Hz), 7.93–7.88 (m, 3H), 7.72 (dd, 1H, J=1.8, 8.7 Hz), 7.63–7.54 (m, 3H), 7.07 (d, 2H, J=8.7 Hz), 7.03 (d, 2H, J=8.7 Hz), 4.16–4.06 (m, 3H), 2.88–2.71 (m, 6H); FAB MS m/z 627 (M+1).

EXAMPLE 187

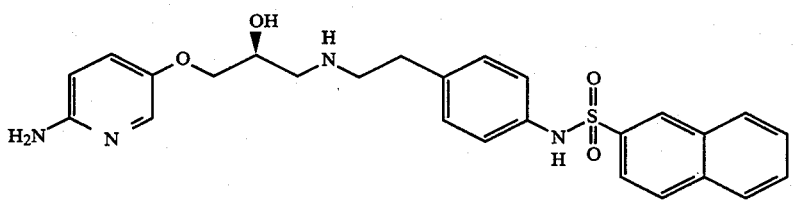

(S)-N-[4-[2-[[3-[(2-amino-5-pyridinyl)oxy]-2-hydroxypropyl]amino]-ethyl]phenyl]-2-naphthalenesulfonamide A solution of 31.1 mg (0.0496 mmol) of the benzenazo derivative from Example 186 in 2 mL of acetic acid and 2 mL of methanol was stirred over 20% palladium hydroxide on carbon under an atmosphere of hydrogen for 1h. It was then filtered and concentrated. Purification by flash chromatography (silica gel, 10% 10:1 methanol:concentrated ammonium hydroxide in dichloromethane) gave 19.0 mg (78%) of the title compound: ¹H NMR (400 MHz, CD₃OD) δ8.27 (d, 1H, J=1.8 Hz), 7.93–7.87 (m, 3H), 7.72 (dd, 1H, J =1.8, 8.7 Hz), 7.62–7.54 (m, 3H), 7.17 (dd, 1H, J=3.0, 9.0 Hz), 7.06–7.01 (overlapping d, 4H), 6.55 (d, 1H, J=9.2 Hz), 3.95 (m, 1H), 3.86–3.79 (overlapping dd, 2H), 2.82–2.63 (m, 6H); FAB MS m/z 493 (M+1).

EXAMPLE 188

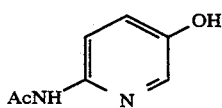

2-Acetamido-5-hydroxypyridine

A mixture of 1.72 g (10.4 mmol) of 2-acetamido-5-methoxypyridine, prepared according to the procedure of J. Lombardino, *J. Med. Chem.* 1981, 24, 39–42, and 2.54 g (51.8 mmol) of sodium cyanide in 10 mL of DMSO was heated at 165° C. under nitrogen for 48 h. The mixture was concentrated under vacuum to remove the DMSO. Purification by flash chromatography (silica, crude product transferred to column in methanol, then diluted with dichloromethane and eluted with 10% 10:1 methanol:concentrated aqueous ammonium hydroxide in dichloromethane) gave 0.881 g (56%) of the title compound as a brown solid: ¹H NMR (400 MHz, CD₃OD) δ7.84–7.81 (overlapping d, 2H), 7.19 (dd, 1H, J=2.9, 8.9 Hz), 2.12 (s, 3H).

EXAMPLE 189

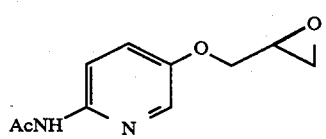

(S)-2-[(2-Acetamidopyridin-5-yl)methyl]oxirane

To a solution of 842 mg (5.53 mmol) of 2-acetamido-5-hydroxypyridine from Example 188 in 15 mL of DMF at 0° C. was added 221 mg (5.53 mmol) of sodium hydroxide as a 60% dispersion in oil. After the mixture was allowed to stir for 30 min, 1.58 g (6.09 mmol, 1.1 equiv) of (2S-glycidyl 3-nitrobenzene sulfonate was added. The reaction mixture was stirred at room temperature for 4 h, then partitioned between 400 mL of ethyl acetate and 100 mL of saturated aqeous sodium chloride solution. The aqueous layer was washed with 100 mL of ethyl acetate. The combined organic phases were dried over magnesium sulfate and concentrated under high vacuum to remove DMF. Purification by flash chromatography (silica, 80% ethyl acetate/hexane) gave 716 mg (62%) of the title compound as a crystalline solid: ¹H NMR (400 MHz, CDCl₃) δ8.11 (d, 1H, J=9.1 Hz), 7.98 (br s, 1H), 7.95 (d, 1H, J=2.9 Hz), 4.26 (dd, 1H, J=2.9, 11.0 Hz), 3.92 (d, 1H, J=5.8, 11.0 Hz), 3.33 (m, 1H), 2.90 (t, 1H, J=4.5 Hz), 2.74 (dd, 1H, J=2.6, 4.8 Hz), 2.16 (s, 3H).

EXAMPLE 190

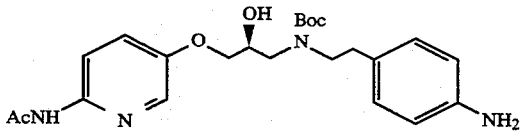

(S)-N-[2-[4-(Aminophenyl)]ethyl]-2-hydroxy-3-[(2-acetamidopyridin-5-yl)oxy]propylcarbamic acid 1,1-dimethylethyl ester In a manner analogous to that of Examples 163 and 164, the title compound was prepared from the epoxide from Example 189: $^1$H NMR (400 MHz, CD$_3$OD) δ7.93–8.02 (m, 2H), 7.38 (d, 1H, J=8Hz), 6.89–6.98 (m, 2H), 6.66 (d, 2H, 10 Hz), 4.06 (m, 1H), 3.89–4.00 (m, 2H), 3.38–3.50 (m, 3H), 3.14 (m, 1H), 2.70 (t, 2H,J=8Hz), 2.13 (s, 3H), 1.41 (s, 9H).

EXAMPLE 191

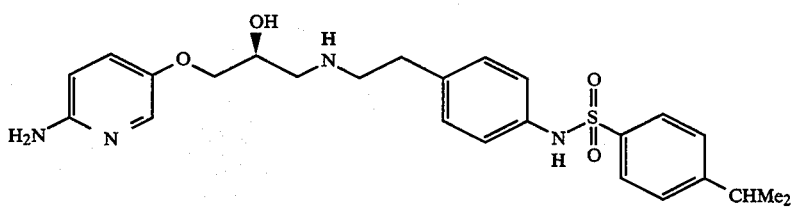

(S)-N-[4-[2-[[3[(2-amino-5-pyridinyl)oxy]-2-hydroxypropyl]amino]-ethyl]-phenyl]-4-isopropylbenzenesulfonamide To a solution of the BOC-protected aniline from Example 190 (1.16 g, 2.6 mmol) and pyridine (300 μL, 3.64 mmol, 1.4 eq) in 45 mL of methylene chloride was added 4-isopropylbenzenesulfonyl chloride (577 mg, 2.6 mmol). The reaction mixture was stirred at room temperature under nitrogen atmosphere overnight. The pink solution was poured into brine (20 mL) and the organics were extacted with methylene chloride. The solution was washed with saturated ammonium chloride solution, water and brine and then dried over anhydrous magnesim sulfate. The solution was filtered and concentrated under vacuum. Purification by flash column chromatography (silica gel, ethyl acetate) gave 1.54 g (94.5%) of the corresponding N-acetyl derivative: $^1$H NMR (400 MHz, CD$_3$OD) δ7.94–8.00 (m, 2H), 7.60–7.67 (m, 2H), 7.37 (d, 1H, J=10 Hz), 7.31 (d, 2H, J=10 Hz), 6.98–7.08 (m, 4H), 4.06 (m, 1H), 3.89–4.00 (m, 2H), 3.35–3.50 (m, 3H), 3.11 (m, 1H), 2.91 (m, 1H), 2.76 (t, 2H, J=8 Hz), 2.13 (s, 3H), 1.38 (d, 9H), 1.20 (d, 6H, J=8 Hz).

A solution of the N-acetyl derivative (1.54 g, 2.46 mmol) in 30 mL of methanol with 20 mL of 2 N hydrochloric acid was refluxed at 90° C. for 20 h. The solvent was stripped under vacuum and the residue was purified by flash column chromatography (silica gel, 90:10:1 methylene chloride/methanol/30% ammonium hydroxide) to give 970 mg (83 %) of the titled compound. $^1$H NMR (400 MHz, CD$_3$OD) δ7.64 (d, 2H, J=8 Hz), 7.60 (d, 1H, J=2 Hz), 7.32 (d, 2H, J =8 Hz), 7.19 (dd, 1H, J=2.10 Hz), 7.08 (d, 2H, J=8 Hz), 7.00 (d, 2H, J=8 Hz), 6.56 (d, 1H, J=10 Hz), 3.98 (m, 1H), 3.81–3.89 (m, 2H), 2.92 (hept, 1H, J=8 Hz), 2.65–2.86 (m, 6H), 1.21 (d, 6H, J=8 Hz).FAB-MS m/e 485 (M+1).

Following procedures outlined for Examples 185–191, the compounds listed in Table 7 were prepared.

TABLE 7

| Example | R | Selected $^1$H NMR (CD$_3$OD) Data |
|---|---|---|
| 192 | 4-bromophenyl | 7.61(d, 2H, J=9.3Hz), 7.59(d, 2H, J=9.3Hz) |
| 193 | 4-iodophenyl | 7.83(d, 2H, J=8.6Hz), 7.43(d, 2H, J=8.6Hz) |
| 194 | 3,4-dichlorophenyl | 7.61–7.58(m, 3H) |
| 195 | 4-methoxyphenyl | 7.64(d, 2H, J=8.9Hz), 6.94(d, 2H, J=8.9Hz), 3.80(s, 3H) |
| 196 | 4-aminophenyl | 7.38(d, 2H, J=8.9Hz), |
| 197 | 4-phenylphenyl | 6.56(d, 2H, J=8.8Hz) 7.78(d, 2H, J=8.6Hz), 7.69(d, 2H, J=8.6Hz), 7.62–7.59(m, 3H), 7.43(t, 2H, J=7.4Hz), 7.37(t, 1H, J=7.2Hz) |
| 198 | 4-CH$_2$CH$_2$Ph | 7.26–7.14(m, 8H), 3.27(m, 2H), 3.03(m, 2H) |
| 199 | naphth-1-yl | 8.72(d, 1H, J=8.7Hz), 8.14(d, 1H, J=7.3Hz), 8.06(d, 1H, J=8.3Hz), 7.95(d, 1H, J=8.7Hz), 7.67(dt, 1H, J=1.5, 8.6Hz), 7.61–7.57(m, 2H), 7.47(t, 1H, J=7.8Hz) |
| 200 | 6-methoxynaphth-2-yl | 8.20(d, 1H, J=1.8Hz), 7.83(d, 1H, J=5.4Hz), 7.81(d, 1H, J=5.4Hz), 7.68(dd, 1H, J=1.1, 8.8Hz), 7.60(d, 1H, J=2.6Hz), 7.18(m, 1H), 3.91(s, 3H) |
| 201 | quinolin-3-yl | 9.01(d, 1H, J=2.2Hz), 8.74(d, 1H, J=2.2Hz), 8.06(m, 2H), 7.95(apparent dt, 1H), 7.73(apparent t, 1H) |
| 202 | 1,3-benzodioxol-5-yl | 7.77(dd, 1H, J=10.5, 3.5Hz), 7.3(dd, 1H, J=9.5, 2Hz), 7.14(d, 1H, J=2Hz), 6.03(s, 2H) |
| 203 | 1,4-benzodioxan-6-yl | 7.54(s, 1H), 7.49(d, 1H, J=8Hz), 4.25(m, 5H) |
| 204 | 2-methylthiobenzothiazol-5-yl | 8.09(s, 1H), 7.86(d, 1H, J=8.0Hz), 7.63(d, 1H, J=8.0Hz), 2.73(s, 3H) |
| 205 | benzothiophen-2-yl | 7.83(t, 2H, J=7.2), 7.71(s, 1H), 7.40(m, 2H) |
| 206 | 1,2-benzisoxazol-5-yl | 7.82–7.78(m, 3H) |

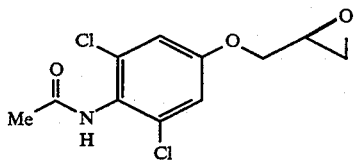

(S)-2-[(4-acetamido-3,5-dichlorophenoxy)methyl]oxirane

4-Acetamido-3,5-dichlorobenzenediazonium tetrafluoroborate was converted to the corresponding phenol according to the procedure of T. Cohen, et. al., *J. Org. Chem.*, 42, 2053–2058 (1977). Thus, 22 g (94 mmol) of copper (II) nitrate was dissolved in 100 mL of water and 300 mg (0.94 mmol) of 4-acetamido-3,5-dichlorobenzenediazonium tetrafluoroborate was added. Copper (I) oxide (405 mg, 2.8 mmol) was added. The mixture was stirred for 35 min, then filtered through Celite, diluted with 1N aqueous sodium bisulfate, and extracted with 4 portions of dichloromethane and 8 portions of ethyl acetate. The combined organic phases were dried over magnesium sulfate and concentrated. Purification by flash chromatography (silica, 50% ethyl acetate/hexanes) gave 72 mg (35%)of 4-acetamido-3,5-dichlorophenol. This compound was convened to the title compound in a manner analogous to that of Example 1: $^1$H NMR (400 MHz, CDCl$_3$) δ6.97 (s, 2H), 4.21 (dd, 1H), 3.86 (dd, 1H), 3.32 (m, 1H), 2.91 (t, 1H), 2.73 (dd, 1H), 2.20 (s, 3H).

EXAMPLE 208

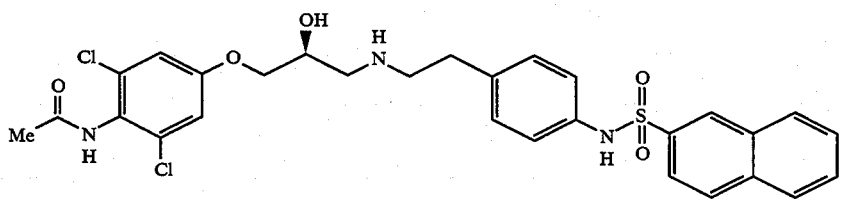

(S)-N-[4-[2-[[2-hydroxy-3-(4-acetamido-3,5-dichlorophenoxy)propyl]amino]ethyl]phenyl]-2-naphthalenesulfonamide The Cbz amine from Example 13 was deprotected as described in Example 6. In a manner analogous to that of Example 7, the title compound was prepared from the resultant amine and the epoxide from Example 207: $^1$H NMR (400 MHz, CD$_3$OD) δ8.28 (d, 1H, J=1.7 Hz), 7.95–7.90 (m, 3H), 7.72 (dd, 1H, J=1.9, 8.7 Hz), 7.63–7.57 (m, 2H), 7.09–7.02 (m, 6H), 4.02 (m, 1H), 3.97–3.88 (overlapping dd, 2H), 2.89–2.72 (m, 6H), 2.15 (s, 3H).

EXAMPLE 209

(S)-N-[4-[2-[[2-hydroxy-3-(4-amino-3,5-dichlorophenoxy)propyl]amino]ethyl]phenyl]-2-naphthalenesulfonamide A solution of 28 mg (0.016 mmol) of the acetamide from Example 208 in 5 mL of methanol and 0.24 mL of 2N aqueous hydrochloric acid was heated at reflux for 3 days. It was then cooled and concentrated. Purification by HPLC (ODS-3, 1:1 methanol:0.1% aqueous trifluoroacetic acid) gave 6.7 mg (13%) the title compound as its bis trifluoracetate salt: $^1$H NMR (400 MHz, CD$_3$OD) δ8.31 (d, 1H, J=1.5 Hz), 7.96–7.90 (m, 3H), 7.75 (dd, 1H, J=1.9, 8.7 Hz), 7.65–7.57 (m, 2H), 7.11 (s, 4H), 6.89 (s, 2H), 4.12 (m, 1H), 3.89 (dd, 1H, J=5.0, 9.9 Hz), 3.85 (dd, 1H, J=5.3, 9.9 Hz), 3.23–3.11 (m, 4 HO, 2.90–2.86 (m, 2H).

EXAMPLE 210

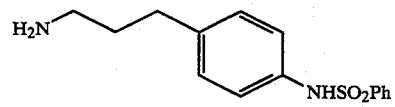

N-[4-(3-aminopropy)phenyl]benzenesulfonamide

A mixture of 0.5g (2.17 mmol) 4-nitrophenethyl bromide and 0.134g (2.71 mmol) of sodium cyanide in dry DMSO was stirred at room temperature for 2 h. The resulting reaction mixture was diluted with water (50 mL) and extracted with methylene chloride twice. The combined organic layers were washed with water, brine, dried over magnesium sulfate and concentrated. The product was isolated by column chromatography on silica gel (15% ethyl acetate/85% Hexanes) to give 0.32 g (84 %) of the 4-nitrophenethyl nitrile.

A 0.3 g-portion (1.7 mmol) of nitro compound in methanol was hydrogenated in the presence of 300 mg of 10% Pd/C until hydrogen uptake ceased. The reaction mixture was tikered and the solvent evaporated from the flitrate. The resultant amine (clean by 1H NMR) was directly used in the next step without any purification.

To a stirred solution of 0.23 g (1.57 mmol) of the resultant amine in methylene chloride (10 mL) at room temperature was added 0.417 g (2.35 mmol) of benzenesulfonyl choride, followed by 0.25 g (3.14 mmol) of pyridine. After 6 h, the reaction mixture was concen-

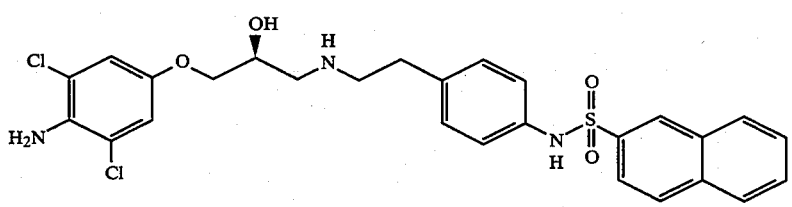

trated and purified on silica (2% methanol/98 methylene chloride) to yield 0.32 g of the sulfonamide nitrile.

To a stirred mixture of 0.318 g (1.1 mmol) of sulfonamide nitrile and 0.53 g (2.22 mmol) of cobalt (II) chloride hexahydrate in methanol (10 mL) was added at room temperature in portions 0.42 g (11 mmol) of sodium borohydride (exothermic). The resulting reaction mixture (black) was stirred at room temperature for 5 h and acidified with 3N hydrochloric acid until the solution become clear. The reaction mixture was concentrated and purified on silica (5% methanol/95 methylene chloride) to give 0.2 g of the amine. $^1$H NMR (400 MHz, CD$_3$OD) 7.73 (dd, 2H), 7.54 m, 1H), 7.45 (m, 2H), 7.06–7.00 (AA', BB', 4H).

EXAMPLE 211

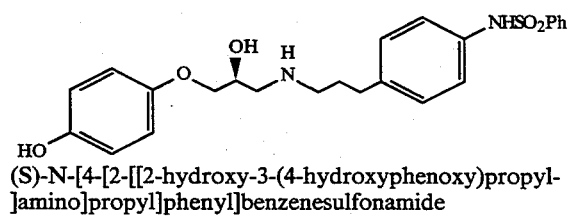

(S)-N-[4-[2-[[2-hydroxy-3-(4-hydroxyphenoxy)propyl]amino]propyl]phenyl]benzenesulfonamide Following the procedures outlined in Examples 7 and 12 the title compound is prepared from the amine from Example 210 and the epoxide from Example 2.

EXAMPLE 212

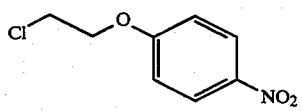

4-Nitrophenyl 2-chloroethyl ether

A solution of 1.611 g of 4-nitro sodium phenoxide (10 mmol), 2.15g (1.25 mL, 15.0 mmol) of 1-bromo-2-chloroethane, and 4.15 g (30.0 mmol) of potassium carbonate in 60 mL of methylethyl ketone was refluxed in an oil bath overnight under nitrogen atmosphere. The reaction was cooled and the solid was filtered off. The filterate was evaporated under vacuum and the residue was purified by flash column chromatography (silica gel, eluant 2:1 hexanes/ethyl acetate) to give 1.35 g (67%) of the title compound: $^1$H NMR (200 MHz, CDCl$_3$) δ8.18 (d, 2H, J=9Hz), 6.95 (d, 2H, J=9Hz), 4.29 (t, 2H, J=6Hz), 3.82 (t, 2H, t=6Hz).

EXAMPLE 213

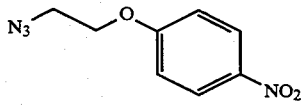

4-nitrophenyl 2-azidoethyl ether

A solution of 1.12 g (5.55 mmol) of 4-nitro 2-chloroethyl ether (Example 212) and lithium azide (544 mg, 11.1 mmol) in 3 mL of DMF was heated at 60° C. in an oil bath overnight under nitrogen atmosphere. The reaction was poured into water and extracted with ethyl acetate. The organics were washed with water and brine and dried over anhydrous magnesium sulfate and concentrated to give 1.12 g (97%) of the product: $^1$H NMR (200 MHz, CDCl$_3$) δ8.18 (d, 2H, J=9Hz), 6.96 (d, 2H, J=9Hz), 4.21 (t, 2H, J=5Hz), 3.63 (t, 2H, J=5Hz).

EXAMPLE 214

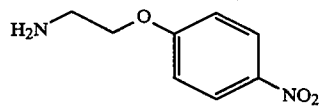

4-Nitrophenyl 2-aminoethyl ether

A solution of 4-nitro 2-aminoethyl ether (610 mg, 2.93 mmol) from Example 213 in 10 mL of THF/water (9:1) was treated with triphenyl phosphine (768 mg, 3.0 mmol) at ambient temperature. After stirring for 3 h, the solvent was removed under vacuum and the residue was purified by flash column chromatography on silica gel (eluant 1:9 methanol/methylene chloride) to give 480 mg (95%) of the title compound: $^1$H NMR (200 MHz, CD$_3$OD) δ8.18 (d, 2H, J=9Hz), 6.96 (d, 2H, J=9Hz), 4.13 (t, 2H, J=5.5Hz), 3.27 (t, 2H, J=5.5Hz).

EXAMPLE 215

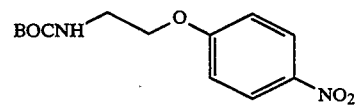

2-(4-Nitrophenoxy)ethylcarbamic acid 1,1-dimethylethyl ester

A solution of 480 mg (2.79 mmol) of amine from Example 214 in 20 mL of methylene chloride was treated with 610 mg (2.80 mmol) of di-tert-butyl dicarbonate. After stirring at room temperature for 40 min., the reaction mixture was concentrated and the resulting yellow solid was used for the next step without further purification: 1H NMR (200 MHz, CDCl$_3$) δ8.15 (d, 2H, J=9Hz), 6.90 (d, 2H, J=9Hz), 4.94 (bs, 1 H, N-H), 4.05 (bt, 2H, J=5.0Hz), 3.50 (q, 2H, J=5.0Hz).

EXAMPLE 216

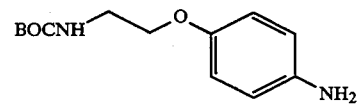

2-(4-Aminophenoxy)ethylcarbamic acid 1,1-dimethylethyl ester

A solution of 775 mg (2.75 mmol) of nitro compound from Example 215 in 20 mL of methanol with 10% palladium on carbon (150 mg) was introduced hydrogen via balloon at room temperature for 4 h. The catalyst was filtered off through Celite, and the filterate was concentrated under vacuum to give 690 mg of the title compound: $^1$H NMR (200 MHz, CDCl$_3$) δ 6.69 (d, 2H, J=8Hz), 6.58 (d, 2H, J=8Hz), 4.94 (bs, 1H, N-H), 3.89 (bt, 2H, J=5.0Hz), 3.40 (q, 2H, J=5.0Hz), 1.40 (s, 9H).

EXAMPLE 217

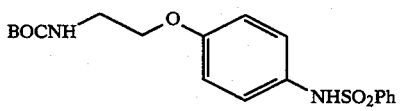

N-[4-[2-[[(1,1-dimethylethoxy)carbonyl]amino]ethoxy]phenyl]benzenesulfonamide

To a solution of 314 mg( 1.246 mmole) of t-BOC amine from Example 216 in 10 mL of methylene chloride was added pyridine (147 mg, 1.869 mmol, 1.5 eq) followed by benzenesulfonyl chloride (242 mg, 1.370 mmol, 1.1 eq) at room temperature. The reaction mixture was stirred at room temperature overnight and then partitioned between water and chloroform. The organic layer was separated and washed with 1N hydrochloric acid, water and brine and then dried over anhydrous sodium sulfate. The solution was filtered, concentrated and the residue was purified by flash colunto chromatography (eluant 2:1 hexanes/ethyl acetate) to give 248 mg (51%) of the product: $^1$H NMR (200 MHz, CDCl$_3$) δ8.01 (d, 1H, J=8Hz), 7.67 (d, 2H, J=8Hz), 6.92 (d, 2H, J=9Hz), 6.72 (s, 1H, N-H), 6.70 (d, 2H, J=9Hz), 4.90 (bs, 1H, N-H), 3.89 (t, 2H, J=5.0Hz), 3.40 (q, 2H, J=5.0Hz), 1.40 (s, 9H).

EXAMPLE 218

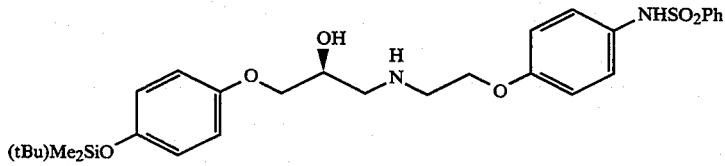

(S)-N-[4-[2-[[2-hydroxy-3-[[4-[[(1,1-dimethylethyl)dimethylsilyl]oxy]phenoxy]propyl]amino]ethyl]oxy]phenyl]benzenesulfonamide A solution of 248 mg (0.632 mmol) of t-BOC amine from Example 217 in 2 mL of methylene chloride was treated with I mL of trifluoroacetic acid for 0.5 h and the reaction mixture was concentrated under vacuum to give the resultant amine (256 mg, 100%) as a trifluoroacetic acid salt. To a solution of this amine in 5 mL of dry methanol was added diisopropylethylamine (90 mg, .70 mmol) followed by the epoxide from example 2 (70 mg, .25 mmol, 0.4 equiv). The reaction was heated at reflux in an oil bath under nitrogen overnight and then cooled to room temperature and concentrated. Purification by preparative thin layer chromatography on silica (eluant 12:88 methanol/methylene chloride) gave 110 mg (77%) of the desired product as a white solid: $^1$H NMR (400 MHz, CDCl$_3$) δ7.65 (dd, 2H, J=8,1Hz), 7.39 (t, 1H, J=7.7Hz), 7.38 (t, 2H, J=7.7 Hz), 6.89 (d, 2H, J=9Hz), 6.70 (s, 4H), 6.69 (d, 2H, J=9Hz), 4.20 (m, 1H), 4.05 (m, 2H), 3.90 (m, 2H), 3.20-3.0 (m, 4H), 0.95 (s, 9H), 0.11 (s, 6H).

EXAMPLE 219

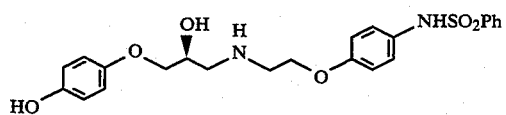

(S)-N-[4-[2-[[2-hydroxy-3-(4-hydroxyphenoxy)propyl]amino]ethoxy]phenyl]benzenesulfonamide In a manner analogous to that of Example 12, the title compound was prepared from the silyl ether from Example 218: $^1$H NMR (200 MHz, CD$_3$OD) δ7.68 (d, 2H,J=8Hz), 7.53 (t, 1H, J=8Hz), 7.43 (t, 2H, J=8 Hz), 7.0 (d, 2H, J=9Hz), 6.86 (d, 2H, J=9Hz), 6.79 (d, 2H, J=9Hz), 6.69 (d, 2H, J=9Hz), 4.21 (m, I H), 3.92 (m, 2H), 3.50 (m, 2H), 3.40-3.20 (m, 4H), EI-MS: calculated for Cl$_{23}$H$_{26}$N$_2$O$_6$S 458; found 459 (M+1).

What is claimed is:

1. A compound having the formula:

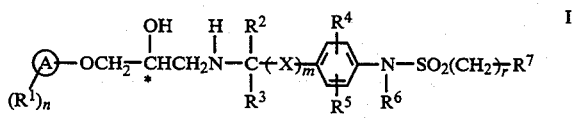

where n is 0 to 7;

m is 0 or 1;

r is 0 to 3;

A is phenyl, naphthyl, a 5 or 6-membered heterocyclic ring with from 1 to 4 heteroatoms selected from oxygen, sulfur or nitrogen, a benzene ring fused to a C$_3$-C$_8$ cycloalkyl ring, a benzene ring fused to a 5 or 6-membered heterocyclic ring with from 1 to 3 heteroatoms selected from oxygen, sulfur or nitrogen or a 5 or 6-membered heterocyclic ring with from 1 to 3 heteroatoms selected from oxygen, sulfur or nitrogen fused to a 5 or 6-membered heterocyclic ring with from 1 to 3 heteroatoms selected from oxygen, sulfur or nitrogen;

R$^1$ is hydroxy, oxo, halogen, cyano, nitro, NR$^8$R$^8$, SR$^8$ trifluoromethyl, C$_1$-C$_6$ alkyl, C$_1$-C$_6$ alkoxy, C$_3$-C$_8$ cycloalkyl, phenyl, SO$_2$R$^9$, NHCOR$^9$, COR$^9$, NR$^8$SO$_2$R$^8$, NR$^8$CO$_2$R$^8$, or C$_1$-C$_6$ alkyl substituted by hydroxy, nitro, halogen, cyano, NR$^8$R$^8$, SR$^8$, trifluoromethyl, C$_1$-C$_6$ alkoxy, C$_3$-C$_8$ cycloalkyl, phenyl, NR$^8$COR$^9$, COR$^9$, SO$_2$R$^9$, NR$^8$SO$_2$R$^9$, NR$^8$CO$_2$R$^8$, or R$^1$ is a 5 or 6-membered heterocycle with from 1 to 3 heteroatoms selected from oxygen, sulfur or nitrogen;

R$^2$ and R$^3$ are independently hydrogen, C$_1$-C$_6$ alkyl or C1-C6 alkyl substituted by 1 to 3 of hydroxy, C$_1$-C$_6$ alkoxy, or halogen;

X is —CH$_2$—, —CH$_2$—CH$_2$—, —CH=CH— or —CH$_2$O—;

$R^4$ and $R^5$ are independently hydrogen, $C_1$–$C_6$ alkyl, halogen, $NHR_8$, $OR_8$, $SO_2R_9$ or $NHSO_2R^9$;

$R^6$ is hydrogen or $C_1$–$C_6$ alkyl;

$R^7$ is $C_3$–$C_8$ cycloalkyl, or B-$(R_1)n$

B is phenyl, naphthyl, a 5 or 6-membered heterocyclic ring with from 1 to 4 heteroatoms selected from oxygen, sulfur or nitrogen, a benzene ring fused to a $C_3$–$C_8$ cycloalkyl ring, a benzene ring fused to a 5 or 6-membered heterocyclic ring with from 1 to 3 heteroatoms selected from oxygen, sulfur or nitrogen or a 5 or 6-membered heterocyclic ring with from 1 to 3 heteroatoms selected from oxygen, sulfur or nitrogen fused to a 5 or 6-membered heterocyclic ring with from 1 to 3 heteroatoms selected from oxygen, sulfur or nitrogen;

$R^8$ is hydrogen, $C_1$–$C_{10}$ alkyl, $C_3$–$C_8$ cycloalkyl, phenyl optionally substituted by 1 to 3 of halogen, $C_1$–$C_6$ alkyl or $C_1$–$C_6$ alkoxy, or $C_1$–$C_{10}$ alkyl substituted by 1 to 3 of hydroxy, halogen, $CO_2H$, $CO_2$-$C_1$–$C_6$ alkyl, $C_3$–$C_8$ cycloalkyl, $C_1$–$C_6$ alkoxy, or phenyl optionally substituted by from 1 to 3 of halogen, $C_1$–$C_6$ alkyl or $C_1$–$C_6$ alkoxy;

$R^9$ is $R^8$, $NHR^8$ or $NR^8R^8$.

2. A compound of claim 1 wherein the 5 and 6-membered heterocycles and fused heterocycles of A, B and $R_1$ are those heterocycles with from 1 to 4 heteroatoms independently selected from one of oxygen or sulfur or 1 to 4 nitrogen atoms.

3. A compound of claim 1 wherein A and B are independently phenyl, naphthyl, or a 5 or 6 membered heterocycle or fused heterocycle with from 1 to 4 heteroatoms independently selected from one of oxygen or sulfur or 1 to 4 nitrogen atoms.

4. A compound of claim 3 wherein A is phenyl, naphthyl, pyridyl, quinolinyl, pyrimidinyl, pyrrollyl, thienyl, imidazolyl or thiazolyl.

5. A compound of claim 3 wherein B is phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzisoxazolyl, benzothiazolyl, tetrahydronaphthyl, dihydrobenzofuranyl, and tetrahydroquinolinyl.

6. A compound of claim 3 wherein $R^2$ and $R^3$ are hydrogen or methyl; X is —$CH_2$—; m is 1; r is 0-2; and $R^5$ and $R^6$ are hydrogen.

7. A compound of claim 3 wherein A is phenyl quinolinyl or a 6-membered heterocyclic ting with 1 or 2 nitrogen atoms;

B is phenyl or quinolinyl;

$R^1$ is $NH_2$, hydroxy, halogen, cyano, trifluoromethyl phenyl, $NR^8COR^9$, $NR^8CO_2R^8$, $C_1$–$C_6$ alkyl optionally substituted by hydroxy; and r is 0 or 2.

8. A compound of claim 1 which is

N-[4-[2-[[2-hydroxy-3-(4-hydroxyphenoxy)propyl-]amino]ethyl]phenyl]benzenesulfonamide N-[4-[2-[[2-hydroxy-3-(4-hydroxyphenoxy)propyl-]amino]ethyl]phenyl]-4-iodobenzenesulfonamide N-[4-[2-[[2-hydroxy-3(4-hydroxyphenoxy)propyl-]amino]ethyl]phenyl]-2-naphthalenesulfonamide N-[4-[2-[[2-hydroxy-3-(4-hydroxyphenoxy)propyl-]amino]ethyl]phenyl]-4-(benzo-2,1,3-thiadiazole)-sulfonamide N-[4-[2-[[2-hydroxy-3-(4-hydroxyphenoxy)propyl-]amino]ethyl]phenyl]-2phenylethanesulfonamide N-[4-[2-[[3-(4-fluorophenoxy)-2-hydroxypropyl-]amino]ethyl]phenyl]-4-benzenesulfonamide N-[4-[2-[[3-[(2-amino-5-pyridinyl)oxy]-2-hydroxypropyl]amino]ethyl]phenyl]-2-naphthalenesulfonamide N-[4-[2-[[2-hydroxy-3-(4-hydroxyphenoxy)propyl-]amino]ethyl]phenyl]-3-quinolinesulfonamide N-[4-[2-[[2-hydroxy-3-(4-hydroxyphenoxy)propyl-]amino ]ethyl]phenyl]4-[(5-methoxycarbonyl)pentanoyl]amino]benzenesulfonamide N-[4-[2-[[2-hydroxy-3-(4-hydroxyphenoxy)propyl-]amino]ethyl]phenyl]-4-[(5-hydroxycarbonyl)pentanoyl]amino]benzenesulfonamide N-[4-[2-[[2-hydroxy-3-(4-hydroxyphenoxy)propyl-]amino]ethyl]phenyl]-4-(hexylaminocarbonylamino)benzenesulfonamide N-[4-[2-[(2-hydroxy-3-phenoxypropyl)amino]ethyl]-phenyl]-4-chlorobenzenesulfonamide N-[4-[2-[[2-hydroxy-3-(3-cyanophenoxy)propyl-]amino]ethyl]phenyl]-3quinolinesulfonamide N-[4-[2-[[3-(4-amino-3-cyanophenoxy)-2-hydroxypropyl]amino]ethyl]phenyl]-3-quinolinesulfonamide N-[4-[2-[[2-hydroxy-3-[(3-hydroxymethyl)phenoxy]-propyl]amino]ethyl]phenyl]-3-quinolinesulfonamide N-[4-[2-[[2-hydroxy-3-(3-pyridyloxy)propyl]amino]ethyl]phenyl]-3-quinolinesulfonamide N-[4-[2-[[2-hydroxy-3-(3-pyridyloxy)propyl]amino]ethyl]phenyl]-4-iodobenzenesulfonamide N-[4-[2-[[3-[(2-amino-5-pyridinyl)oxy]-2-hydroxypropyl]amino]ethyl]phenyl]-4-isopropylbenzenesulfonamide.

9. A compound of claim 1 with the structural formula:

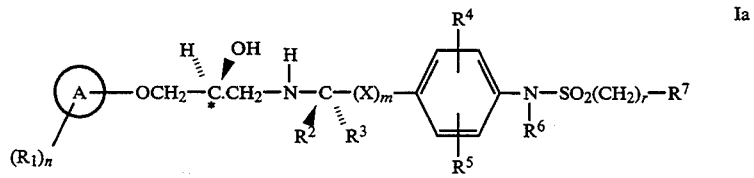

Ia where n, m, r, A, $R_1$, $R_2$, $R_3$, $R_4$, $R_5$, $R_6$, $R_7$ and X are as defined in claim 1.

10. A process for the preparation of a compound of claim 1 which comprises treating a compound having the formula:

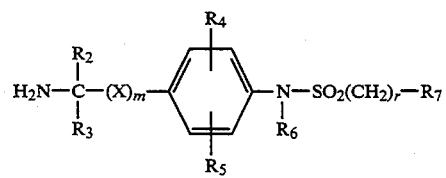

with a compound having the formula:

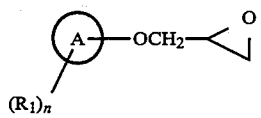

where n, m, r, A, $R_1$, $R_2$, $R_3$, $R_4$, $R_5$, $R_6$, $R_7$ and X are as defined in claim 1.

11. A method for the treatment of diabetes which comprises administering to a diabetic patient an effective amount of a compound of claim 1.

12. A method for the treatment of obesity which comprises administering to an obese patient an effective amount of a compound of claim 1.

13. A method for lowering triglyceride levels and cholesterol levels of raising high density lipoprotein levels which comprises administering to a patient needing lower triglyceride and cholesterol levels or higher high density lipoprotein levels an effective amount of a compound of claim 1.

14. A method for decreasing gut motility which comprises administering to a patient in need of decreased gut motility, an effective amount of a compound of claim 1.

15. A method for reducing neurogenic inflammation of airways which comprises administering to a patient in need of reduced neurogenic intimation, an effective amount of a compound of claim 1.

16. A method for reducing depression which comprises administering to a depressed patient an effective amount of a compound of claim 1.

17. A method for treating gastrointestinal disorders which comprises administering to a patient with gastrointestinal disorders an effective amount of a compound of claim 1.

18. A composition for the treatment of diabetes or obesity or for lowering triglyceride or cholesterol levels or increasing high density lipoprotein levels or for decreasing gut motility or for reducing neurogenic intimation or for treating depression or for treating gastrointestinal disorders which comprises an inert carder and an effective amount of a compound of claim 1.

* * * * *